United States Patent
Price et al.

(10) Patent No.: US 11,278,306 B2
(45) Date of Patent: *Mar. 22, 2022

(54) SURGICAL INSTRUMENT WITH ORIENTATION SENSING

(71) Applicant: Ethicon LLC, Guaynabo, PR (US)

(72) Inventors: Daniel W. Price, Loveland, OH (US); Sora Rhee, Pennsylvania Furnace, PA (US); Cory G. Kimball, Hamilton, OH (US); Timothy G. Dietz, Reading, MA (US); Ashvani K. Madan, Mason, OH (US); Donna L. Korvick, San Antonio, TX (US); Jeffrey D. Messerly, Cincinnati, OH (US); William E. Clem, Bozeman, MT (US); Jacqueline C. Aronhalt, Loveland, OH (US); William D. Dannaher, Cincinnati, OH (US); John B. Schulte, West Chester, OH (US); Danius P. Silkaitis, Seattle, WA (US); Stephen J. Balek, Springboro, OH (US); Michael R. Lamping, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 157 days.

This patent is subject to a terminal disclaimer.

(21) Appl. No.: 16/266,598

(22) Filed: Feb. 4, 2019

(65) Prior Publication Data

US 2019/0239918 A1 Aug. 8, 2019

Related U.S. Application Data

(63) Continuation of application No. 15/420,654, filed on Jan. 31, 2017, now Pat. No. 10,327,798, which is a
(Continued)

(51) Int. Cl.
*A61B 17/32* (2006.01)
*A61B 18/14* (2006.01)
(Continued)

(52) U.S. Cl.
CPC .......... *A61B 17/320092* (2013.01); *A61B 17/320068* (2013.01); *A61B 18/1445* (2013.01);
(Continued)

(58) Field of Classification Search
CPC .... A61B 17/320092; A61B 17/320068; A61B 2090/0814; A61B 2090/064; A61B 2034/2048
See application file for complete search history.

(56) References Cited

U.S. PATENT DOCUMENTS 5,400,267 A  3/1995  Denen et al.
5,980,510 A  11/1999  Tsonton et al.
(Continued)

FOREIGN PATENT DOCUMENTS

CN  1670475 A  9/2005
CN  101511293 A  8/2009
(Continued)

OTHER PUBLICATIONS

Chinese Office Action, Notification of the First Office Action, and Search Report dated Jun. 22, 2016 for Application No. CN 201380028273.0, 13 pgs.
(Continued)

*Primary Examiner* — Sarah A Simpson
(74) *Attorney, Agent, or Firm* — Frost Brown Todd LLC

(57) ABSTRACT

A surgical instrument comprises a body assembly and an end effector. The body assembly includes a control module, an orientation sensor communicatively coupled to the control module, and an energy component. The energy component
(Continued)

is operable to activate the end effector at a plurality of energy settings. A storage device is communicatively coupled to the control module and includes a plurality of gesture profiles and corresponding energy settings. The control module is configured to set the energy setting of the energy component to a corresponding energy setting in response to a correlation between the output of the orientation sensor and a gesture profile. In some versions, the control module modifies the energy setting based upon output from a force sensor that measures the force on the end effector. The control module may also decrease the energy setting in response to an anomalous acceleration or deceleration detected by an accelerometer.

20 Claims, 11 Drawing Sheets

Related U.S. Application Data continuation of application No. 13/484,584, filed on May 31, 2012, now Pat. No. 9,572,592.

(51) Int. Cl.
| | | |
|---|---|---|
| A61B 34/20 | (2016.01) | |
| A61B 90/00 | (2016.01) | |
| A61B 17/00 | (2006.01) | |
| A61B 18/00 | (2006.01) | |

(52) U.S. Cl.
CPC ............. *A61B 2017/0046* (2013.01); *A61B 2017/00115* (2013.01); *A61B 2017/00207* (2013.01); *A61B 2017/00473* (2013.01); *A61B 2017/320093* (2017.08); *A61B 2017/320094* (2017.08); *A61B 2017/320095* (2017.08); *A61B 2017/320097* (2017.08); *A61B 2018/00702* (2013.01); *A61B 2018/00898* (2013.01); *A61B 2018/00988* (2013.01); *A61B 2034/2048* (2016.02); *A61B 2090/064* (2016.02); *A61B 2090/0814* (2016.02); *F04C 2270/041* (2013.01)

(56) References Cited

U.S. PATENT DOCUMENTS

| | | | |
|---|---|---|---|
| 6,494,882 B1 | 12/2002 | Lebouitz et al. | |
| 6,500,176 B1 | 12/2002 | Truckai et al. | |
| 6,660,017 B2 | 12/2003 | Beaupre | |
| 6,783,524 B2 | 8/2004 | Anderson et al. | |
| 6,849,814 B2 | 2/2005 | Ogden | |
| 6,908,472 B2 | 6/2005 | Wiener et al. | |
| 6,972,199 B2 | 12/2005 | Lebouitz et al. | |
| 7,235,072 B2* | 6/2007 | Sartor | A61B 18/1402 606/34 |
| 7,367,973 B2 | 5/2008 | Manzo et al. | |
| 7,416,101 B2 | 8/2008 | Shelton, IV et al. | |
| 7,738,971 B2 | 6/2010 | Swayze et al. | |
| 7,749,240 B2 | 7/2010 | Takahashi et al. | |
| 8,419,757 B2 | 4/2013 | Smith et al. | |
| 8,461,744 B2 | 6/2013 | Wiener et al. | |
| 8,657,174 B2 | 2/2014 | Yates et al. | |
| 8,939,974 B2 | 1/2015 | Boudreaux et al. | |
| 8,986,302 B2 | 3/2015 | Aldridge et al. | |
| 9,011,471 B2 | 4/2015 | Timm et al. | |
| 9,023,071 B2 | 5/2015 | Miller et al. | |
| 9,364,249 B2 | 6/2016 | Kimball et al. | |
| 9,510,895 B2 | 12/2016 | Houser et al. | |
| 9,572,592 B2 | 2/2017 | Price et al. | |
| 10,327,798 B2 | 6/2019 | Price et al. | |
| 2004/0034340 A1 | 2/2004 | Biscup | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0292691 A1 | 11/2010 | Brogna | |
| 2012/0110810 A1 | 5/2012 | Houser et al. | |
| 2012/0116391 A1 | 5/2012 | Houser et al. | |
| 2012/0203213 A1* | 8/2012 | Kimball | A61B 17/320068 606/1 |
| 2013/0253480 A1* | 9/2013 | Kimball | A61B 17/320092 606/1 |
| 2013/0289561 A1* | 10/2013 | Waaler | A61B 18/1477 606/42 |
| 2013/0324991 A1 | 12/2013 | Clem et al. | |

FOREIGN PATENT DOCUMENTS

| | | |
|---|---|---|
| CN | 102458286 A | 5/2012 |
| DE | 102009042438 A1 | 3/2011 |
| EP | 0432122 A2 | 6/1991 |
| JP | S50-110258 U | 9/1975 |
| JP | 2002-360602 A | 12/2002 |
| JP | 2004-504097 A | 2/2004 |
| JP | 2005-066316 A | 3/2005 |
| JP | 2006-518262 A | 8/2006 |
| JP | 2008-061962 A | 3/2008 |
| JP | 2013-505090 A | 2/2013 |
| WO | WO 1998/025666 A1 | 6/1998 |
| WO | WO 2000/065659 A1 | 11/2000 |
| WO | WO 2010/140462 A1 | 11/2012 |

OTHER PUBLICATIONS

Chinese Search Report, Supplementary, dated Mar. 28, 2017 for Application No. CN 201380028273.0, 1 pg.
Japanese Office Action, Notification of Reasons for Refusal, dated Mar. 14, 2017 for Application No. JP 2015-515093, 6 pgs.
International Search Report and Written Opinion dated Nov. 22, 2013 for Application No. PCT/US2013/042664.
International Preliminary Report on Patentability dated Dec. 2, 2014 for Application No. PCT/US2013/042664.
Indian Examination Report dated Aug. 18, 2020 for Application No. 10609/DELNP/2014, 5 pgs.

* cited by examiner

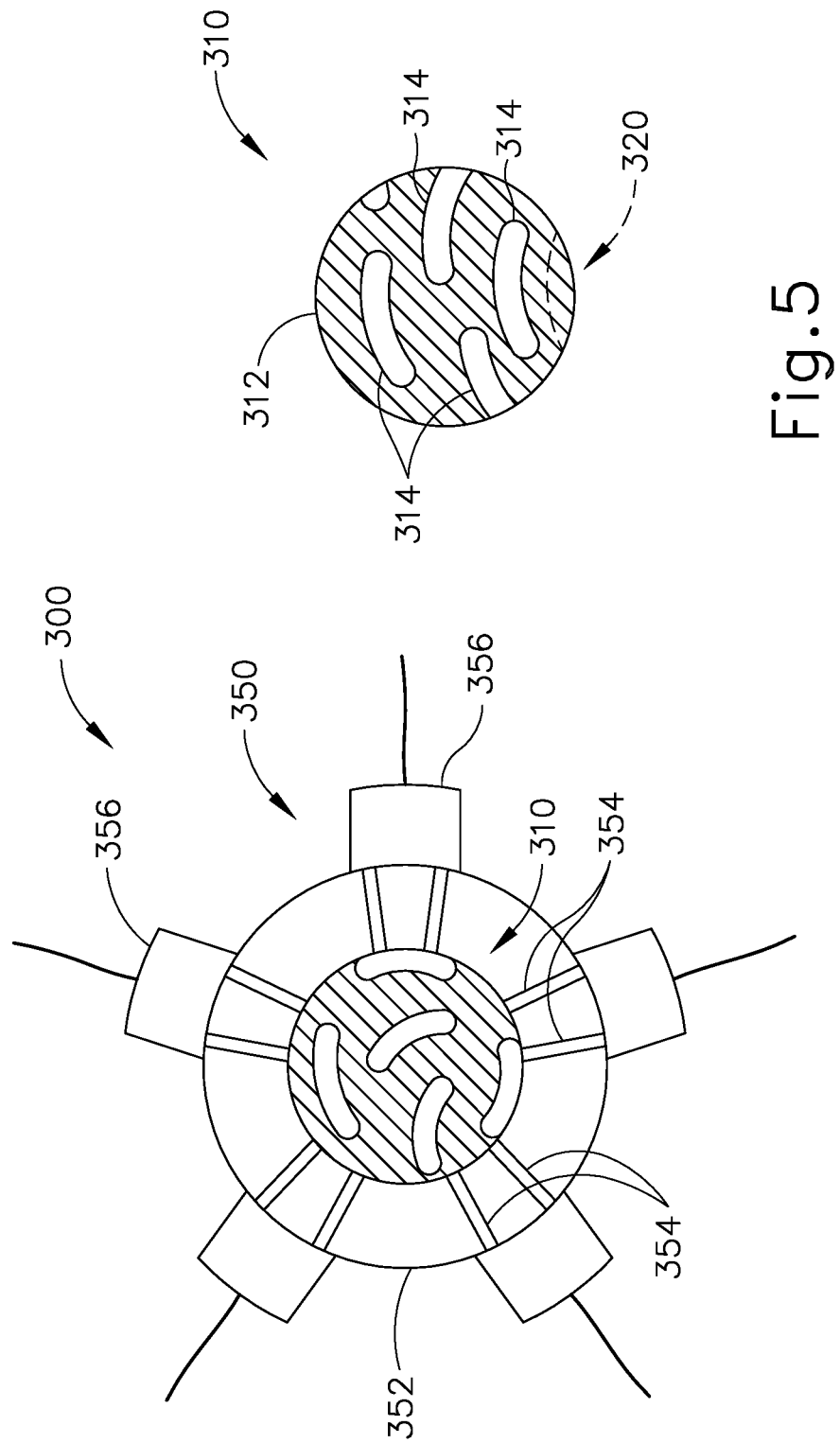

SURGICAL INSTRUMENT WITH ORIENTATION SENSING

This application is a continuation of U.S. application Ser. No. 15/420,654, filed Jan. 31, 2017, published as U.S. Pub. No. 2017/0196585 on Jul. 13, 2017, issued as U.S. Pat. No. 10,327,798 on Jun. 25, 2019, entitled "Surgical Instrument with Orientation Sensing," which is a continuation of U.S. application Ser. No. 13/484,584, filed May 31, 2012, issued as U.S. Pat. No. 9,572,592 on Feb. 21, 2017, entitled "Surgical Instrument with Orientation Sensing."

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. In some situations, a user may need to use the instrument a number of times prior to effectively and efficiently using such devices to perform various procedures. This adaptation time may make some users avoid adopting the use of new instruments. Accordingly, it may be useful to provide a surgical instrument with various user aides to decrease the learning curve for how to use the instrument.

Examples of such endoscopic surgical instruments that may be adapted to include such user interface aides may include those disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007 now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,174, issued Feb. 25, 2014, the disclosure of which is incorporated by reference herein; and U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, some of the foregoing surgical tools may include a cordless transducer such as that disclosed in U.S. Pat. Pub. No. 2009/0143797, entitled "Cordless Hand-held Ultrasonic Cautery Cutting Device," published Jun. 4, 2009 now U.S. Pat. No. 8,419,757, issued Apr. 16, 2013, the disclosure of which is incorporated by reference herein.

Some of the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While a variety of devices and methods have been made and used for endoscopic surgical procedures, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a partial side cross-sectional view of an exemplary orientation sensor having a conductive sphere disposed within a sensor casing;

FIG. 5 depicts a side elevation view of the conductive sphere of FIG. 4 showing a plurality of conductive sections and a weight;

Figure 1:
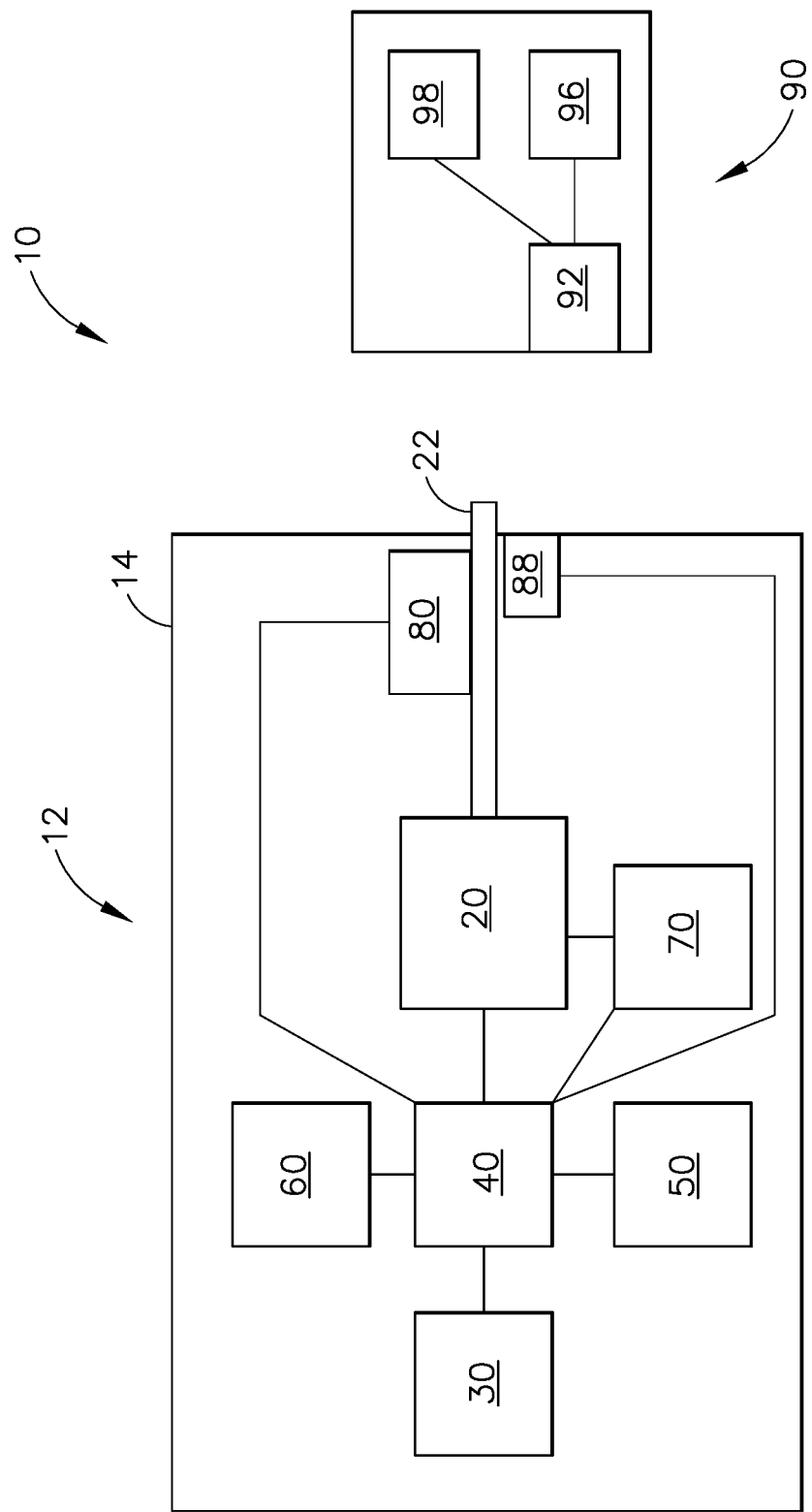
FIG. 1 depicts a block schematic of an exemplary surgical instrument having one or more orientation sensors.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 depicts an exemplary surgical instrument (10) comprising a handle assembly (12) and a detachable end effector (90). Of course it should be understood that in some versions end effector (90) may be fixedly coupled to handle assembly (12) or to a shaft (22). In the present example, handle assembly (12) comprises a casing (14) that includes an energy component (20), a first sensor (30), a control module (40), a storage device (50), a user interface (60), a power source (70), a second sensor (80), and a first connector (88). In the present example, energy component (20) is coupled to power source (70) and is operable to activate end effector (90). By way of example only, energy component (20) may comprise an ultrasonic transducer having a shaft (22) that is operable to transmit ultrasonic motion to a blade of end effector (90) when end effector (90) is coupled to shaft (22) and/or handle assembly (12). One example is described in U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. In other versions, energy component (20) may comprise a motor or other component operable to transmit motion to one or more components of end effector (90) via shaft (22) and/or otherwise. One merely exemplary motor driven surgical instrument is disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein. Of course in some versions energy component (20) and/or shaft (22) may be omitted entirely and power source (70) may be operable to directly activate one or more features of end effector (90). For example, power source (70) may be operable to transmit RF energy to end effector (90) such as that disclosed in U.S. Pat. No. 6,500,176 entitled "Electrosurgical Systems and Techniques for Sealing Tissue," issued Dec. 31, 2002, the disclosure of which is incorporated by reference herein. While power source (70) is depicted in the present example as contained within handle assembly (12) (e.g., as one or more rechargeable batteries), it should be understood that power source (70) may be external to handle assembly (12), such a generator (120) shown in FIG. 2. Of course still further configurations for energy component (20) and/or power source (70) will be apparent to one of ordinary skill in the art in view of the teachings herein.

As shown in FIG. 1, control module (40) is communicatively coupled to energy component (20), first sensor (30), storage device (50), user interface (60), power source (70), second sensor (80), and first connector (88). Of course it should be understood that any of the foregoing components may be omitted and/or not communicatively coupled to control module (40); and that control module (40) may be in communication with a variety of other components in addition to or in lieu of those described herein. Control module (40) comprises an integrated circuit or a microcontroller configured to receive input from one or more components, such as sensors (30, 80, 98), storage device (50), and/or end effector storage device (96); and output control instructions to one or more components and/or devices, such as energy component (20) and/or user interface (60), though the output is merely optional (e.g., control module (40) may merely be a diagnostic tool to receive information or the components and/or devices may be integrated with control module (40) such that control module (40) may directly activate or deactivate components and/or devices). In some versions, control module (40) further comprises EEPROM to store data thereon. For instance, the EEPROM may store machine readable code to control various components of surgical instrument (10) or the EEPROM may contain one or more operational settings and/or modes stored in data tables. Of course other machine readable code and/or configurations for the EEPROM will be apparent to one of ordinary skill in the art in view of the teachings herein. Such code could also be stored in storage device (50), as described below. In the present example, control module (40) is integrated into surgical instrument (10) though this is merely optional. In some versions, control module (40) may be integrated into generator (120) (shown in FIG. 2) and communicatively coupled to instrument (10) via cable (130) or control module (40) may be an independent device communicatively coupled to instrument (10). Of course still further configurations for control module (40) will be apparent to one of ordinary skill in the art in view of the teachings herein.

First sensor (30) of the present example comprises a sensor operable to detect the orientation and/or movement of instrument (10). By way of example only, first sensor (30) may comprise a gyroscopic sensor, an inclinometer, an accelerometer, and/or any other suitable orientation and/or movement sensor as will be apparent to one of ordinary skill in the art in view of the teachings herein. As shown in FIG. 1, first sensor (30) is communicatively coupled to control module (40) and is operable to transmit signals to control module (40) indicative of the orientation and/or motion of instrument (10) relative to a baseline orientation and/or motion. Of course it should be understood that first sensor (30) may be configured to provide information in addition, or in the alternative, to orientation and/or movement of instrument (10). Some merely exemplary alternative sensors include heat sensors such as those described in U.S. Non-provisional Pat. Appln. No. 13/277,328, entitled "Surgical Instrument with Sensor and Powered Control," filed Oct. 20, 2011, now U.S. Pat. No. 9,782,214, issued Oct. 10, 2017, the disclosure of which is incorporated by reference herein. Of course first sensor (30) is merely optional and may be omitted or integrated into other components, such as control module (40). Still further sensors (30) will be apparent to one of ordinary skill in the art in view of the teachings herein.

Storage device (50) is communicatively coupled to control module (40) and is operable to store or retrieve data for control module (40). Storage device (50) comprises a computer readable medium that is capable of storing data or instructions in a form in which they can be retrieved and/or processed by control module (40). A computer readable medium should not be limited to any particular type or organization, and should be understood to include distributed and decentralized systems however they are physically or logically disposed, as well as storage objects of systems which are located in a defined and/or circumscribed physical and/or logical space. By way of example only, storage device (50) may include hard discs, read only memory, random access memory, solid state memory elements, optical discs, and/or registers. As will be described in greater detail below, storage device (50) may include one or more configuration datas for instrument (10). Such configuration datas may be used with the data provided from first sensor (30), second sensor (80), and/or end effector sensor (98) by control module (40) to determine whether the user is using instrument (10) in accordance with the expected usage and/or to adjust the output from energy component (20) based upon how the user is using instrument (10). Of course storage device (50) is merely optional and may be omitted or integrated into other components, such as control module (40) and/or generator (120). Still further configurations for storage device (50) will be apparent to one of ordinary skill in the art in view of the teachings herein.

User interface (60) is also communicatively coupled to control module (40) such that control module (40) may control user interface (60). It should be understood that user interface (60) can comprise a component that only communicates information to a user, is operable to receive input from a user, or both. For example, user interface (60) may include a speaker that is operable to emit audible tones. By way of example only, control module (40) may be configured to output varying tones from the speaker in response to whether the user is using instrument (10) in accordance with an expected usage when compared to a configuration data, as will be described in greater detail below. In addition, or in the alternative, user interface (60) may include LEDs or other visual components such that control module (40) can operate the LEDs or other visual components. Further still, user interface (60) may include a simple screen or a touchscreen. The screen may be operable to display one or more graphical outputs indicative of whether the user is using instrument (10) in the proper manner. Further still, a touchscreen may be operable to select one or more of the configuration datas, to select a type of surgical procedure, and/or to select other options or features for instrument (10). Yet a further version may include input buttons or other input components such that a user may manage control module (40) or other components of instrument (10). Of course two or more of the foregoing may be combined for user interface (60). For instance, user interface (60) may include a speaker and a plurality of LEDs. In another version, user interface (60) may include a speaker and a screen displaying a graphical representation of the usage. In yet another version, user interface (60) may include a speaker and a touchscreen that both displays a graphical representation of the usage and is operable to select one or more of the configuration datas and/or to select other options or features for instrument (10). Still further user interfaces (60) will be apparent to one of ordinary skill in the art in view of the teachings herein. In addition, in some versions user interface (60) may be omitted.

Second sensor (80) of the present example comprises a sensor operable to detect the orientation of force applied to end effector (90) of instrument (10) or a vector of force applied by tissue against end effector (90). By way of example only, second sensor (80) may comprise one or more strain gauges coupled to shaft (22) extending between energy component (20) and end effector (90). In some versions, a plurality of strain gauges may be positioned about shaft (22) to determine the orientation of the force. In addition, second sensor (80) may be used to also determine the magnitude of force applied to end effector (90). Second sensor (80) may be constructed in accordance with at least some of the teachings of U.S. Pat. No. 9,681,884, entitled "Surgical Instrument with Stress Sensor," issued Jun. 20, 2017, the disclosure of which is incorporated by reference herein. Of course still further sensors as will be apparent to one of ordinary skill in the art in view of the teachings herein. As shown in FIG. 1, second sensor (80) is communicatively coupled to control module (40) and is operable to transmit signals to control module (40) indicative of the force applied to shaft (22) and/or end effector (90) of instrument (10). Of course it should be understood that second sensor (80) may be configured to provide information in addition, or in the alternative, to the force applied to shaft (22) and/or end effector (90). Some merely exemplary alternative sensors include heat sensors such as those described in U.S. Non-provisional Pat. Appln. No. 13/277,328, entitled "Surgical Instrument with Sensor and Powered Control," filed Oct. 20, 2011, now U.S. Pat. No. 9,782,214, issued Oct. 10, 2017, the disclosure of which is incorporated by reference herein. Still further sensors (80) will be apparent to one of ordinary skill in the art in view of the teachings herein. Of course it should be understood that second sensor (80) may also be omitted in some versions.

First connector (88) is communicatively coupled to control module (40) and is operable to electrically and communicatively couple end effector (90) to control module (40). For example, first connector (88) may comprise a plurality of electrical contacts that are configured to couple to a plurality of electrical contacts of second connector (92) of end effector (90). Of course first connector (88) may have other configurations (e.g., inductive coupling) that are operable to electrically and/or communicatively couple to end effector (90). In some versions, such as those where end effector (90) is fixedly coupled to handle assembly (12), first connector (88) may be omitted entirely.

End effector (90) of the present example detachably couples to handle assembly (12) and is coupled to energy component (20) via shaft (22). Merely exemplary ways to couple end effector (90) to handle assembly (12) include clips, clamps, snaps, threads, hook and loop connectors, etc. In addition, or in the alternative, end effector (90) may be constructed in accordance with at least some of the teachings of U.S. Pat. Appln. No. 13/269,870, entitled "Surgical Instrument with Modular Shaft and End Effector," filed Oct. 10, 2011, now U.S. Pat. No. 9,510,895, issued Dec. 6, 2016, the disclosure of which is incorporated by reference herein. As with energy component (20) noted above, end effector (90) may be configured to engage tissue in a number of ways to achieve a diagnostic or therapeutic effect (e.g., endocutter, grasper, cutter, stapler, clip applier, access device, drug/gene therapy delivery device, and energy delivery device using ultrasonic vibrations, RF, laser, etc.). By way of example only, end effector (90) may be constructed in accordance with at least some of the teachings of U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; and U.S. Pat. No. 6,500,176 entitled "Electrosurgical Systems and Techniques for Sealing Tissue," issued Dec. 31, 2002, the disclosure of which is incorporated by reference herein. Of course still other configurations for end effector (90) will be apparent to one of ordinary skill in the art in view of the teachings herein.

End effector (90) includes second connector (92), an end effector storage device (96), and an end effector sensor (98). As noted above, second connector (92) comprises a plurality of electrical contacts that are configured to electrically and communicatively couple end effector (90) to control module (40) when end effector (90) is attached to handle assembly (12). End effector storage device (96) of the present example comprises a computer readable medium that is capable of storing data or instructions in a form in which they can be retrieved and/or processed by control module (40). The computer readable medium should not be limited to any particular type or organization, and should be understood to include distributed and decentralized systems however they are physically or logically disposed, as well as storage objects of systems which are located in a defined and/or circumscribed physical and/or logical space. By way of example only, end effector storage device (96) may include hard discs, read only memory, random access memory, solid state memory elements, optical discs, and/or registers. In the present example, end effector storage device (96) comprises a non-volatile memory module that is communicatively coupled to second connector (92) such that end effector storage device (96) is communicatively coupled to control module (40) when end effector (90) is coupled to handle assembly (12). Of course other configurations for end effector storage device (96) will be apparent to one of ordinary skill in the art in view of the teachings herein. Further still, in some versions, end effector storage device (96) may be omitted entirely.

End effector sensor (98) of the present example comprises a sensor operable to detect the orientation and/or movement of end effector (90). By way of example only, end effector sensor (98) may comprise a gyroscopic sensor, an inclinometer, an accelerometer, and/or any other suitable orientation and/or movement sensor as will be apparent to one of ordinary skill in the art in view of the teachings herein. As shown in FIG. 1, end effector sensor (98) is communicatively coupled to control module (40) via the interface of first and second connectors (88, 92), and end effector sensor (98) is operable to transmit signals to control module (40) indicative of the orientation and/or motion of end effector (90) relative to a baseline orientation and/or motion. Of course it should be understood that end effector sensor (98) may be configured to provide information in addition, or in the alternative, to orientation and/or movement of end effector (90). For instance, end effector sensor (98) may be configured to detect a force applied to a blade (not shown) of end effector (90) and may be constructed in accordance with at least some of the teachings of second sensor (80) described above. In addition, or in the alternative, some merely exemplary other sensors include heat sensors such as those described in U.S. Non-provisional Pat. Appln. No. 13/277,328, entitled "Surgical Instrument with Sensor and Powered Control," filed Oct. 20, 2011, now U.S. Pat. No. 9,782,214, issued Oct. 10, 2017, the disclosure of which is incorporated by reference herein. Still further end effector sensors (98) will be apparent to one of ordinary skill in the art in view of the teachings herein. Moreover, it should be understood that in some versions, end effector sensor (98) may be omitted entirely.

II. Exemplary Surgical Systems and Surgical Instruments

While the foregoing block schematic generally describes a surgical instrument (10) that is coupleable to an end effector (90) and includes a variety of components to provide feedback to control module (40), various configurations for surgical instrument (10) and/or surgical systems will now be described.

A. Exemplary Elongated Ultrasonic Surgical Instrument with Pistol Grip

Figure 2:
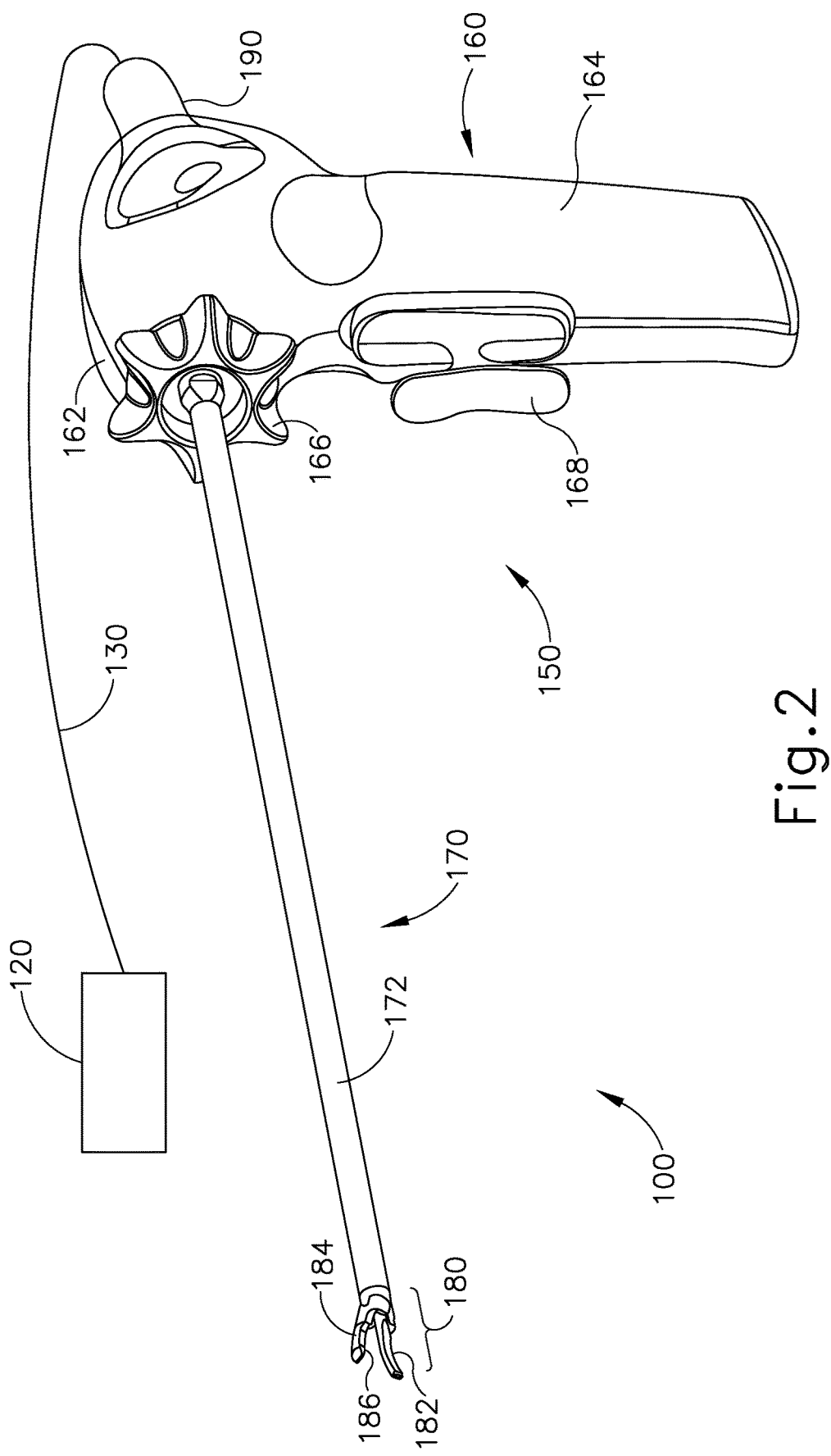
FIG. 2 depicts a perspective view of an exemplary surgical instrument.

FIG. 2 shows an exemplary ultrasonic surgical system (100) that may incorporate one or more of the components described above. In the present example, system (100) comprises an ultrasonic surgical instrument (150), a generator (120), and a cable (130) operable to couple generator (120) to surgical instrument (150). A suitable generator (120) is the GEN 300 sold by Ethicon Endo-Surgery, Inc. of Cincinnati, Ohio. By way of example only, generator (120) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. Generator (120) may include one or more of control module (40), storage device (50), user interface (60), and/or power supply (70) described above, though these are merely optional. It should be noted that surgical instrument (150) is described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example is described in reference to a cable-connected surgical instrument (150), it should be understood that surgical instrument (150) may be adapted for cordless operation, such as that disclosed in U.S. Pat. Pub. No. 2009/0143797, entitled "Cordless Hand-held Ultrasonic Cautery Cutting Device," published Jun. 4, 2009 now U.S. Pat. No. 8,419,757, issued Apr. 16, 2013, the disclosure of which is incorporated by reference herein. Furthermore, surgical device (150) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (150) of the present example includes a multi-piece handle assembly (160), an elongated transmission assembly (170), and a transducer (190). It should be understood that surgical instrument (150) may be viewed as an exemplary version of surgical instrument (10) described above. Transmission assembly (170) is coupled to multi-piece handle assembly (160) at a proximal end of transmission assembly (170) and extends distally from multi-piece handle assembly (160). In the present example transmission assembly (170) is configured to be an elongated, thin tubular assembly for endoscopic use, but it should be understood that transmission assembly (170) may alternatively be a short assembly, such as those shown in FIGS. 3, 6, and 9-11, and/or those disclosed in U.S. Pat. Pub. No. 2007/0282333, entitled "Ultrasonic Waveguide and Blade," published December 6, 2007, now abandoned, and U.S. Pat. Pub. No. 2008/0200940, entitled "Ultrasonic Device for Cutting and Coagulating," published Aug. 21, 2008, now abandoned, the disclosures of which are incorporated by reference herein. Transmission assembly (170) of the present example comprises an outer sheath (172), an inner tubular actuating member (not shown), a waveguide (not shown), and an end effector (180) located on the distal end of transmission assembly (170). In the present example, end effector (180) comprises a blade (182) coupled to the waveguide, a clamp arm (184) operable to pivot at the proximal end of transmission assembly (170), and, optionally, one or more clamp pads (186) coupleable to clamp arm (184). End effector (180) may be further configured in accordance with end effector (90) described above in reference to FIG. 1. It should also be understood that clamp arm (184) may be omitted if desired.

The waveguide, which is adapted to transmit ultrasonic energy from a transducer (190) to blade (182), may be flexible, semi-flexible, or rigid. In some versions, second sensor (80) may be coupled to the waveguide to detect when force is applied to blade (182) (e.g., as blade (182) bears against tissue). Transducer (190) is an exemplary energy component (20) that may be used. One merely exemplary ultrasonic transducer (190) is Model No. HP054, sold by Ethicon Endo-Surgery, Inc. of Cincinnati, Ohio. It should also be understood that clamp arm (184) and the associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. The waveguide may also be configured to amplify the mechanical vibrations transmitted through the waveguide to blade (182) as is well known in the art. The waveguide may further have features to control the gain of the longitudinal vibration along the waveguide and features to tune the waveguide to the resonant frequency of the system.

In the present example, the distal end of the blade (182) is disposed near an anti-node in order to tune the acoustic assembly to a preferred resonant frequency $f_o$ when the acoustic assembly is not loaded by tissue. When transducer (190) is energized, the distal end of blade (182) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (190) of the present example is activated, these mechanical oscillations are transmitted through the waveguide to end effector (180). In the present example, blade (182), being coupled to the waveguide, oscillates at the ultrasonic frequency. Thus, when tissue is secured between blade (182) and clamp arm (184), the ultrasonic oscillation of blade (182) may simultaneously sever the tissue and denature the proteins in adjacent tissue cells, thereby providing a coagulative effect with relatively little thermal spread. An electrical current may also be provided through blade (182) and clamp arm (184) to also cauterize the tissue. While some configurations for transmission assembly (170) and transducer (190) have been described, still other suitable configurations for transmission assembly (170) and transducer (190) will be apparent to one or ordinary skill in the art in view of the teachings herein.

Multi-piece handle assembly (160) of the present example comprises a mating housing portion (162) and a lower portion (164). Mating housing portion (162) is configured to receive transducer (190) at a proximal end of mating housing portion (162) and to receive the proximal end of transmission assembly (170) at a distal end of mating housing portion (162). An aperture is provided on the distal end of mating housing portion (162) for insertion of various transmission assemblies (170). A rotation knob (166) is shown in the present example to rotate transmission assembly (170) and/or transducer (190), but it should be understood that rotation knob (166) is merely optional. Mating housing portion (162) and/or transmission assembly (170) may be further constructed in accordance with at least some of the teachings of U.S. Pat. Appln. No. 13/269,870, entitled "Surgical Instrument with Modular Shaft and End Effector," filed Oct. 10, 2011, now U.S. Pat. No. 9,510,895, issued Dec. 6, 2016, the disclosure of which is incorporated by reference herein. Lower portion (164) of multi-piece handle assembly (160) includes a trigger (168) and is configured to be grasped by a user using a single hand. One merely exemplary alternative configuration for lower portion (164) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. It should be understood that various components included handle assembly (12) may be incorporated into multi-piece handle assembly (160).

In addition, while multi-piece handle assembly (160) has been described in reference to two distinct portions (162, 164), it should be understood that multi-piece handle assembly (160) may be a unitary assembly with both portions (162, 164) combined. Multi-piece handle assembly (160) may alternatively be divided into multiple discrete components, such as a separate activation portion (operable either by a user's hand or foot) and a separate mating housing portion (162). The activation portion may be operable to activate transducer (190) and may be remote from mating housing portion (162). Multi-piece handle assembly (160) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (160) will be apparent to those of ordinary skill in the art in view of the teachings herein. For instance, instrument (150) may be operated as part of a robotic system. Other configurations for multi-piece handle assembly (160) will also be apparent to those of ordinary skill in the art in view of the teachings herein. By way of example only, surgical instrument (150) may be constructed in accordance with at least some of the teachings of U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757.

B. Exemplary Handheld Ultrasonic Surgical Instrument with Pencil Grip

Figure 3:
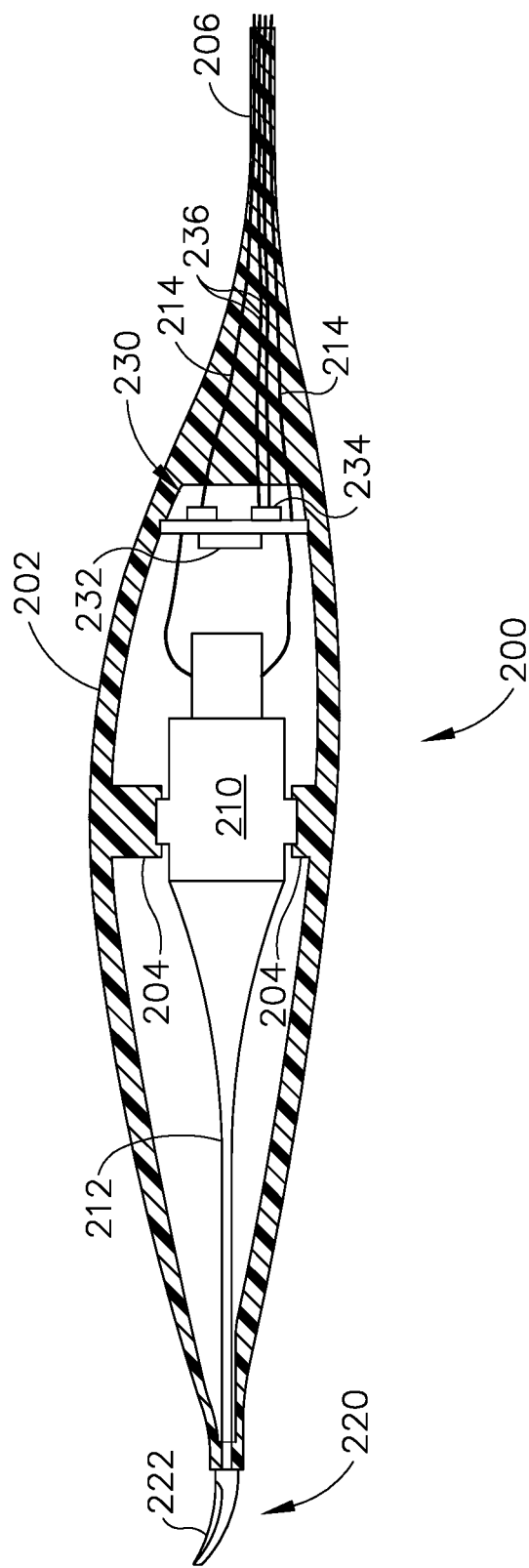
FIG. 3 depicts a side cross-sectional view of a second exemplary surgical instrument showing a first exemplary orientation sensor assembly.

FIG. 3 depicts an alternative surgical instrument (200) that is configured to be held in the hand of a user similar to a pen or pencil. Surgical instrument (200) may also be viewed as another exemplary version of surgical instrument (10) described above. As shown in the present example, instrument (200) comprises a casing (202), a rotatable transducer (210), an end effector (220), and an orientation sensor assembly (230). Casing (202) is sized and configured to contain transducer (210) and orientation sensor assembly (230) therein. Casing (202) may be constructed from a durable plastic (such as polycarbonate or a liquid crystal polymer), ceramics and/or metals or any other suitable material as will be apparent to one of ordinary skill in the art in view of the teachings herein. Transducer (210) is rotatably mounted to casing (202) via mounts (204). Transducer (210) is electrically coupled to a generator (not shown), such as generator (120), via wires (214) that extend through a proximal end of casing (202) and a cable (206). Transducer (210) also includes a waveguide (212) extending distally to end effector (220). Transducer (210) may be further constructed in accordance with at least some of the teachings for transducer (190) above and/or otherwise.

End effector (220) is coupled to a distal end of casing (202) and includes a blade (222) that is coupled to waveguide (212). Accordingly, when transducer (210) is energized, the distal end of blade (222) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. Thus, when blade (222) is applied against tissue, the ultrasonic oscillation of blade (222) may simultaneously sever the tissue and denature the proteins in adjacent tissue cells, thereby providing a coagulative effect with relatively little thermal spread. In some versions, end effector (220) is detachably coupled to casing (202) such that various end effectors (220) can be used with instrument (200). Of course other configurations for end effector (220) will be apparent to one of ordinary skill in the art in view of the teachings herein.

Orientation sensor assembly (230) is mounted within casing (202) and includes one or more sensors (232, 234) configured to sense the orientation and/or movement of instrument (200). In the present example, orientation sensor assembly (230) comprises an integrated circuit or a microcontroller having a gyroscope (232) and an accelerometer (234). By way of example only, orientation sensor assembly (230) may comprise a MEMS (microelectromechanical system) gyroscope/accelerometer. Orientation sensor assembly (230) is electrically coupled to a control module (not shown) via wires (236). In some versions, the control module may be integrated into the generator while, in others, the control module may be a separate device. In still other versions, the control module may be integrated with orientation sensor assembly (230). Of course it should be understood that one or more components of instrument (10) may also be incorporated into instrument (200). Gyroscope (232) of the present example is operable to provide orientation data relative to a baseline orientation. Merely exemplary baseline orientations may include instrument (200) at a longitudinal orientation, as shown in FIG. 3, a vertical orientation perpendicular to that shown in FIG. 3, and/or any other orientation. Accelerometer (234) is operable to provide movement of instrument (200) relative to a stationary position and/or other state of inertia. Accordingly, with gyroscope (232) and accelerometer (234), the orientation and movement of instrument (200) may be determined. Of course other configurations for orientation sensor assembly (230) will be apparent to one of ordinary skill in the art in view of the teachings herein.

III. Exemplary Alternative Orientation Sensors

While the foregoing describes a first sensor (30) and a gyroscope (232) that are operable to sense the orientation of the foregoing instruments (10, 150, 200), it should be understood that other orientation sensors may be used with instruments (10, 150, 200, 400, 500, 600). Moreover, in some instances instruments (10, 150, 200, 400, 500, 600) may be configured to be reusable via resterilization by an autoclave. In such cases, conventional electronic components may not survive the resterilization process. Accordingly, various alternative orientation sensors that can survive the resterilization process may be preferable. While some of the exemplary sensors described below may survive various resterilization processes, such functionality need not necessarily be incorporated into all versions of such sensors.

One merely exemplary alternative orientation sensor (300) is shown in FIGS. 4-5. As shown in FIG. 4, sensor (300) comprises an orb (310) and a casing (350). Orb (310) rotates and/or spins substantially freely within casing (350). Referring to FIG. 5, orb (310) comprises a sphere (312) and a plurality of conductive paths (314) disposed on the exterior surface of sphere (312). In the present example, sphere (312) comprises a non-conductive polymer sphere that has a plurality of copper paths (314) overmolded onto sphere (312). Paths (314) are discrete and electrically isolated relative to each other. A weight (320) is provided within one end of sphere (312) such that weight (320) orients the end of sphere (312) downwardly towards the ground via gravity. Thus, even if the orientation of an instrument (10, 150, 200) incorporating orientation sensor (300) is changed, weight (320) maintains the orientation of sphere (312) relative to the ground. Paths (314) of the present example are arranged in a variety of orientations on sphere (312) such that the plurality of paths (314) are configured to engage one or more electrodes (354), as will be described in greater detail below. When orb (310) shifts position within casing (350), the position of orb (310) may be determined by monitoring a plurality of sensors (356) that are electrically coupled to electrodes (354), as will be described in more detail below.

Of course it should be understood that other configurations for orb (310) may be used as well. For instance, paths (314) may further be arranged about sphere (312) such that each path has a unique starting point and ending point relative to the other paths (314). In some versions, a non-conductive material may be placed on paths (314) such that only the starting points and ending points of each path (314) are exposed. Accordingly, paths (314) may be arranged in a wide variety of manners (e.g., L-shaped paths, V paths, overlapping paths with non-conductive material interposed between paths, etc.) such that the position of orb (310) may be determined by monitoring sensors (356). In another version, sphere (312) may comprise a conductive sphere with a layer of non-conductive or insulating material layered on the exterior of sphere (312). Paths (314) may be formed via removal of the non-conductive material such that portions of the conductive sphere (312) are exposed. In yet a further configuration, sphere (312) may simply comprise a conductive sphere and paths (314) may be omitted. In such a version, sphere (312) may be sized to contact only a few electrodes (354) such that the contacted electrodes (354) indicate the position of sphere (312) relative to casing (350). Still further configurations for orb (310) will be apparent to one of ordinary skill in the art in view of the teachings herein.

Referring back to FIG. 4, casing (350) comprises a shell (352) with a plurality of electrodes (354) extending inwardly from shell (352). In the present example, electrodes (354) comprise pogo pins that extend inwardly from shell (352) and that are arranged such that electrodes (354) spherically enclose and contact orb (310). In some versions, the tips of electrodes (354) comprise hemispherically rounded ends. In other versions, electrodes (354) may comprise leaf spring electrodes. Of course any other electrode (354) and/or other geometries of electrodes (354) may be used as will be apparent to one of ordinary skill in the art in view of the teachings herein. In the present example, orb (310) is sized such that each electrode (354) is in contact with orb (310) to always maintain contact between each electrode (354) and some portion of orb (310) regardless of the orientation. Accordingly, a plurality of paths (314) may electrically couple a plurality of electrodes (354) together. In some versions, shell (352) may be filled with a non-conductive fluid to facilitate rotation of orb (310) relative to shell (352) and electrodes (354).

In the present example, two electrodes (354) are coupled to a corresponding sensor (356) such that, when the electrodes (354) are electrically coupled via a path (314) of orb (310), the circuit of sensor (356) is closed. While FIG. 4 depicts five sensors (356) in a plane disposed about orb (310), it should be understood that sensors (356) and electrodes (354) spherically enclose orb (310). Sensors (356) are communicatively coupled to control module (40), shown in FIG. 1, such that control module (40) is operable to read the output from the plurality of sensors (356). Based upon the output from sensors (356), control module (40) may be configured to determine the orientation of instrument (10, 150, 200, 400, 500, 600). By way of example only, a first electrode (354) coupled to a first sensor (356) may have a first voltage applied to it from a power supply, such as power supply (70) and/or generator (120) described above. When path (314) electrically couples this first electrode (354) to a second electrode (354) of sensor (356), sensor (356) outputs the detection of the voltage to control module (40). By way of example only, paths (314), sensors (356), and electrodes (354) may be arranged such that a single path (314) electrically couples electrodes (354) of a single sensor (356) for a given orientation. Accordingly, the orientation of an instrument (10, 150, 200, 400, 500, 600) may be determined based upon which sensor (356) has a closed circuit. Sensors (356), electrodes (354), and paths (314) may be decreased in size and increased in number to provide greater resolution to the orientation of instrument (10, 150, 200, 400, 500, 600). Furthermore, the rate of change between electrical couplings of electrodes (354) and sensors (356) may be measured to provide data on the speed and direction of motion of instrument (10, 150, 200, 400, 500, 600).

Of course other configurations for casing (350) will be apparent to one of ordinary skill in the art in view of the teachings herein. For example, in one alternative version, orb (310) may be sized smaller than the chamber formed by electrodes (354) such that orb (310) only contacts two electrodes (354) at any given orientation. Electrodes (354) may be arranged to alternate between electrodes (354) to which a voltage is applied and electrodes (354) coupled to sensors (356). Accordingly, the orientation of instrument (10, 150, 200, 400, 500, 600) can be determined based upon which sensor (356) has a voltage applied to it. It should be understood that, in the current example, only those electrodes (354) located near the end of orb (310) with weight (320) will be in contact with orb (310). Still other configurations for alternative orientation sensor (300) will be apparent to one of ordinary skill in the art in view of the teachings herein.

Figure 6:
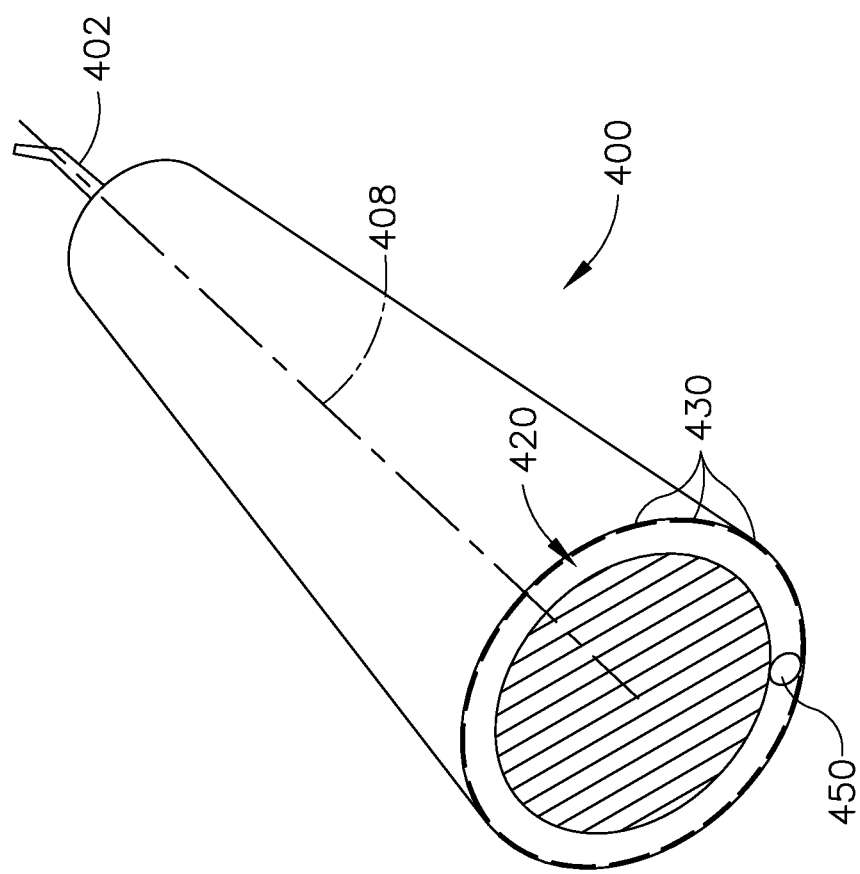
FIG. 6 depicts a rear partial cross-sectional perspective view of an alternative orientation sensor.

FIG. 6 depicts another orientation sensor (410) incorporated into a surgical instrument (400). Sensor (410) of the present example comprises an annular channel (420) formed within instrument (400), a plurality of sensors (430) disposed within channel (420), and a ball (450) sized to roll within channel (420) as the orientation of instrument (400) is changed. Ball (450) of the present example comprises a metallic ball that is sized to fit and travel within channel (420). Of course ball (450) may include a durable polymer based ball (such as polycarbonate or a liquid crystal polymer), ceramics, and/or any other suitable material as will be apparent to one of ordinary skill in the art in view of the teachings herein. Channel (420) of the present example is transversely oriented relative to an end effector (402) of instrument (400) such that sensor (410) is operable to determine the rotational orientation of instrument (400) about a longitudinal axis (408), though this is merely optional. In some versions, channel (420) may be configured to determine the rotational orientation of instrument (400) about a vertical axis (not shown) and/or a lateral axis (not shown). Of course a plurality of channels (420) may be incorporated into instrument (400) and/or channels (420) may have any other orientation, as will be apparent to one of ordinary skill in the art in view of the teachings herein. For example, in some versions three channels (420) corresponding to three orthogonal axes may be provided within instrument (400).

A plurality of sensors (430) are disposed within channel (420) and are configured to detect the position of ball (450) within channel (420). In the present example, sensors (430) comprise force and/or contact sensors configured to detect the weight of ball (450) on sensors (430). It should be understood that ball (450) will roll within channel (420) and will align with the lowest point of channel (420). Accordingly, the sensor (430) that detects ball (450) will approximately indicate the orientation of instrument (400) relative to the longitudinal axis (408). In the present example, sensors (430) are disposed about the circumference of channel (420) such that ball (450) is always touching at least one sensor (430) and, in some cases, two sensors (430). Of course other sensors (430), such as piezoelectric sensors, strain gauges, tactile sensors, load cells, Hall Effect sensors, etc. may be used as will be apparent to one of ordinary skill in the art in view of the teachings herein. In addition, in some versions, the rate of change of sensors (430) indicating the presence of ball (450) may be used to determine the movement of instrument (400). Still further configurations for orientation sensor (410) will be apparent to one of ordinary skill in the art in view of the teachings herein.

IV. Exemplary Detachable End Effector Having Preloaded Gesture Data

Figure 7:
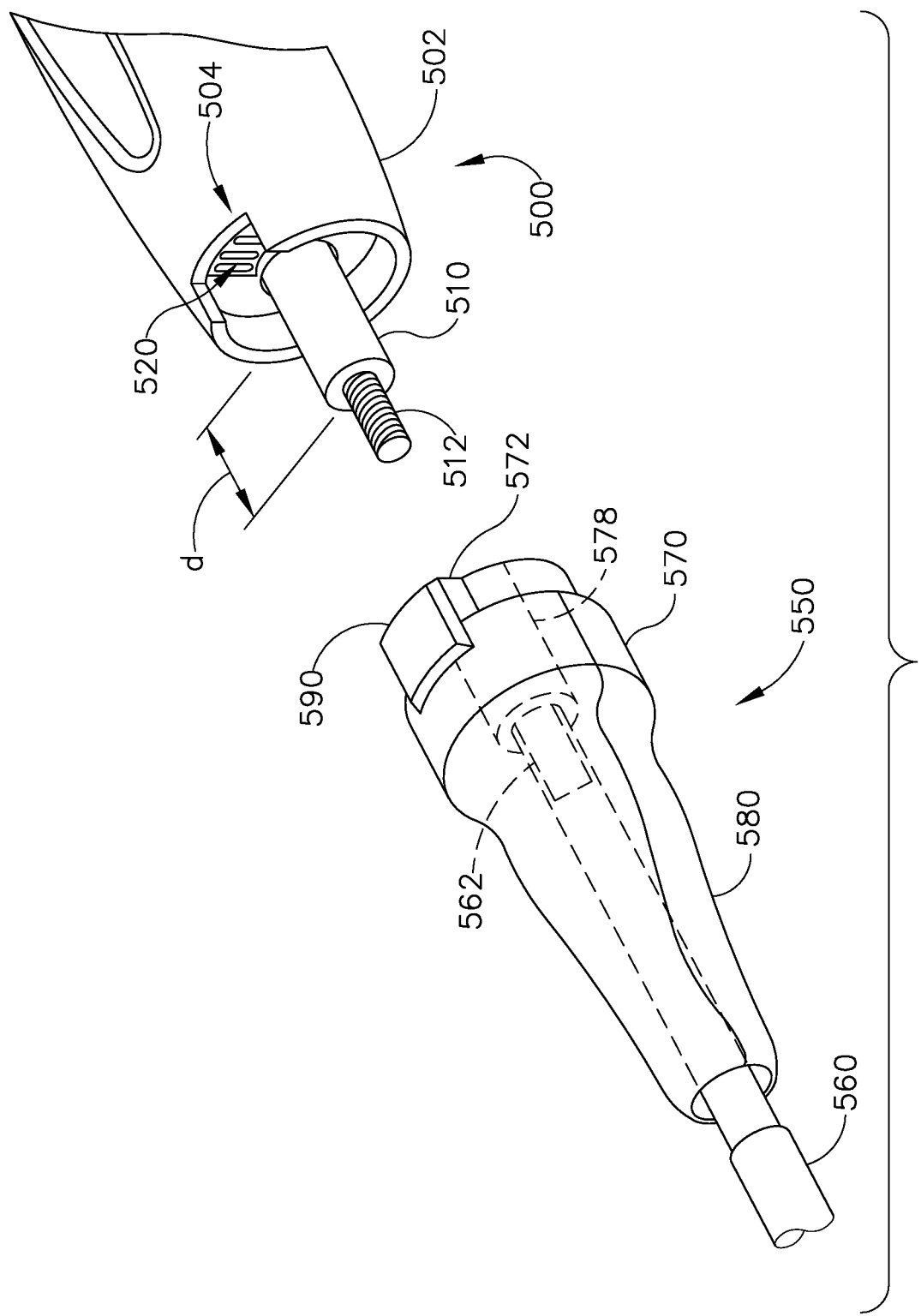
FIG. 7 depicts a partial perspective view of an exemplary detachable end effector cap.

FIG. 7 depicts an end of an exemplary surgical instrument (500) and an exemplary detachable end effector (550). It should be understood that surgical instrument (500) represents still another exemplary variation of surgical instrument (10) described above. In the example shown, instrument (500) comprises a casing (502), a transducer shaft (510) extending from casing (502), and a plurality of electrical contacts (520) on casing (502). Transducer shaft (510) is configured to threadably couple to a waveguide (560) of end effector (550) such that ultrasonic vibrations from a transducer within instrument (500) can be transmitted to a blade (not shown) of end effector (550). In the example shown, transducer shaft (510) includes a threaded portion (512) that begins at a distance d away from a distal most point of casing (502). Distance d corresponds to a longitudinal length of a keyblock (570) such that threaded portion (512) is located within rotation sleeve (580) of end effector (550) when keyblock (570) is coupled to casing (502). Accordingly, waveguide (560) can be threadably coupled to transducer shaft (510) while keyblock (570) is engaged with casing (502). Contacts (520) are metallic members that abut complementary contacts (not shown) on end effector (550) such that one or more components of end effector (550) are electrically coupled to instrument (500). In some versions, contacts (520) are further electrically coupled to a control module, such as control module (40). Of course other electrical coupling features between end effector (550) and instrument (500) will be apparent to one of ordinary skill in the art in view of the teachings herein. In the present example, contacts (520) are disposed within a keyway portion (504) of casing (502) such that end effector (550) can only be coupled to casing (502) in a single orientation. Thus, keyway portion (504) can ensure that contacts (520) are aligned with the complementary contacts of end effector (550). Still further configurations for instrument (500) will be apparent to one of ordinary skill in the art in view of the teachings herein.

End effector (550) comprises waveguide (560), rotation sleeve (580), keyblock (570), and a module (590). In the present example, waveguide (560) is coupled to rotation sleeve (580) such that rotation of rotation sleeve (580) rotates waveguide (560). Waveguide (560) extends distally from rotation sleeve (580) and terminates at a blade (not shown). It should be understood that various features in addition, or in the alternative, to the blade may be included distally of rotation sleeve (580), such as one or more clamp arms. In the example shown, waveguide (560) includes a threaded portion (562) (shown in phantom) to threadably couple waveguide (560) to transducer shaft (510). Thus, when keyblock (570) is engaged with casing (502), as will be described below, rotation sleeve (580) is operable to threadably couple waveguide (560) to transducer shaft (510). Of course further coupling features for waveguide (560) and transducer shaft (510) will be apparent to one of ordinary skill in the art in view of the teachings herein. Keyblock (570) of the present example comprises a key portion (572), a central bore (578) (shown in phantom), and a module (590) mounted to keyblock (570). Central bore (578) is sized and configured to permit transducer shaft (510) to insert through keyblock (570) to engage waveguide (560), as described above. Key portion (572) is configured to insert into keyway portion (504) of casing (502) such that keyblock (570) is rotationally fixed relative to casing (502). Thus, keyblock (570) provides a mechanical ground for rotation sleeve (580) when keyblock (570) is engaged with casing (502). Key portion (572) further includes complementary contacts to contacts (520) described above. The engagement of key portion (572) with keyway portion (504) is configured to rotationally align the set of contacts such that when keyblock (570) is engaged with casing (502), the set of contacts are electrically coupled. The complementary contacts are coupled to module (590) such that module (590) is electrically coupled to contacts (520) when end effector (550) is coupled to instrument (500).

Figure 8:
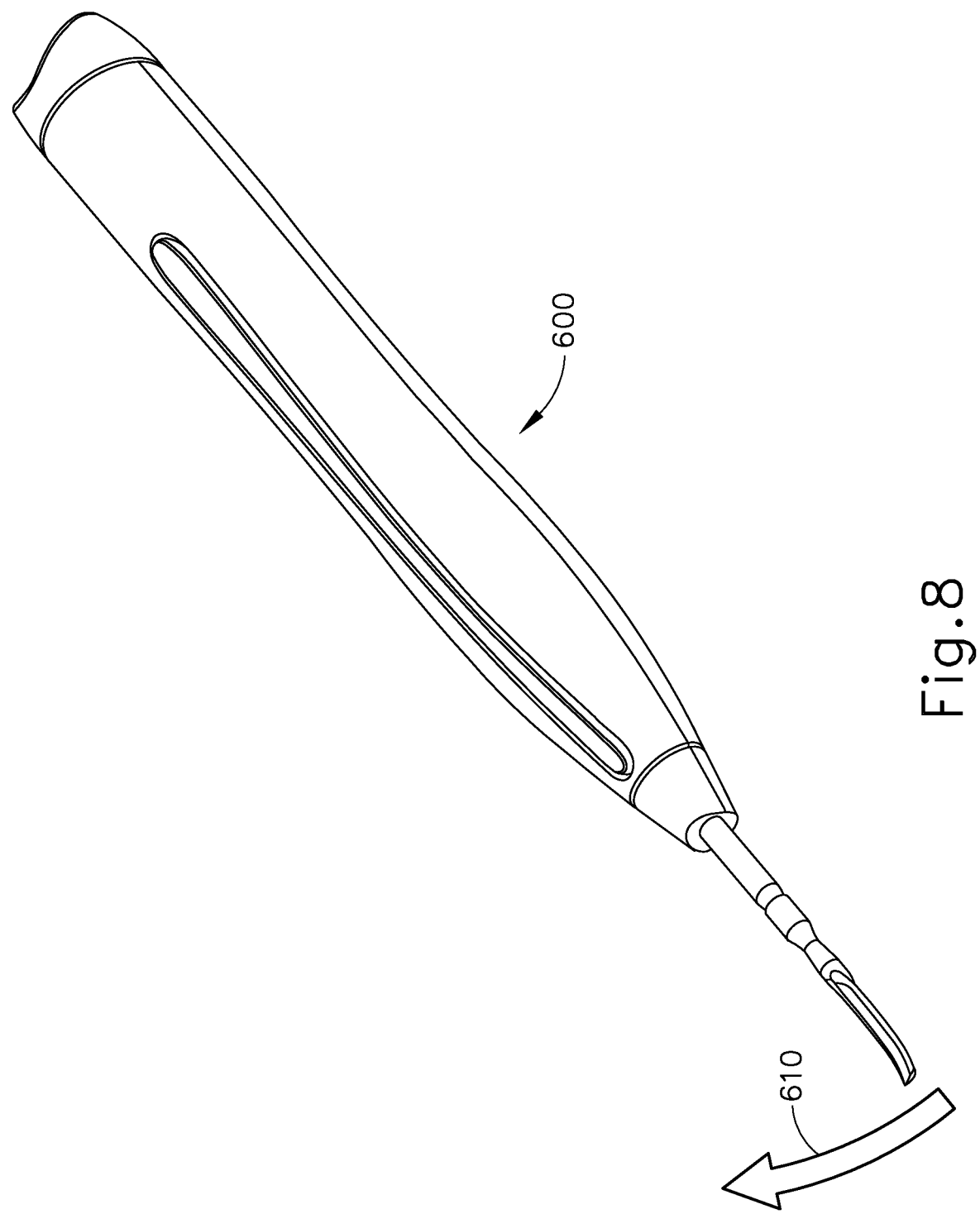
FIG. 8 depicts a perspective view of an exemplary surgical instrument showing a first exemplary gesture.
Figure 9:
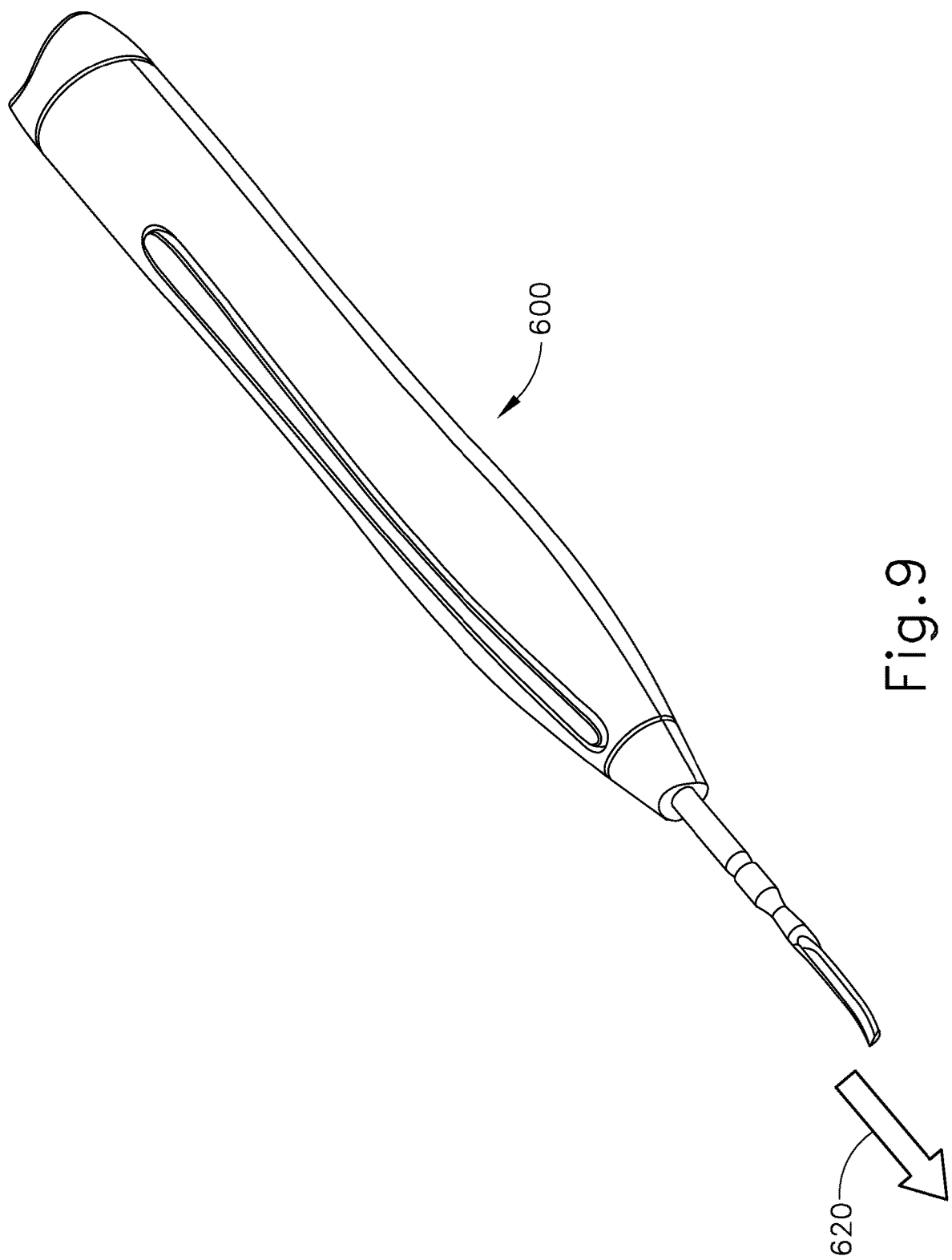
FIG. 9 depicts a perspective view of an exemplary surgical instrument showing a second exemplary gesture.
Figure 10:
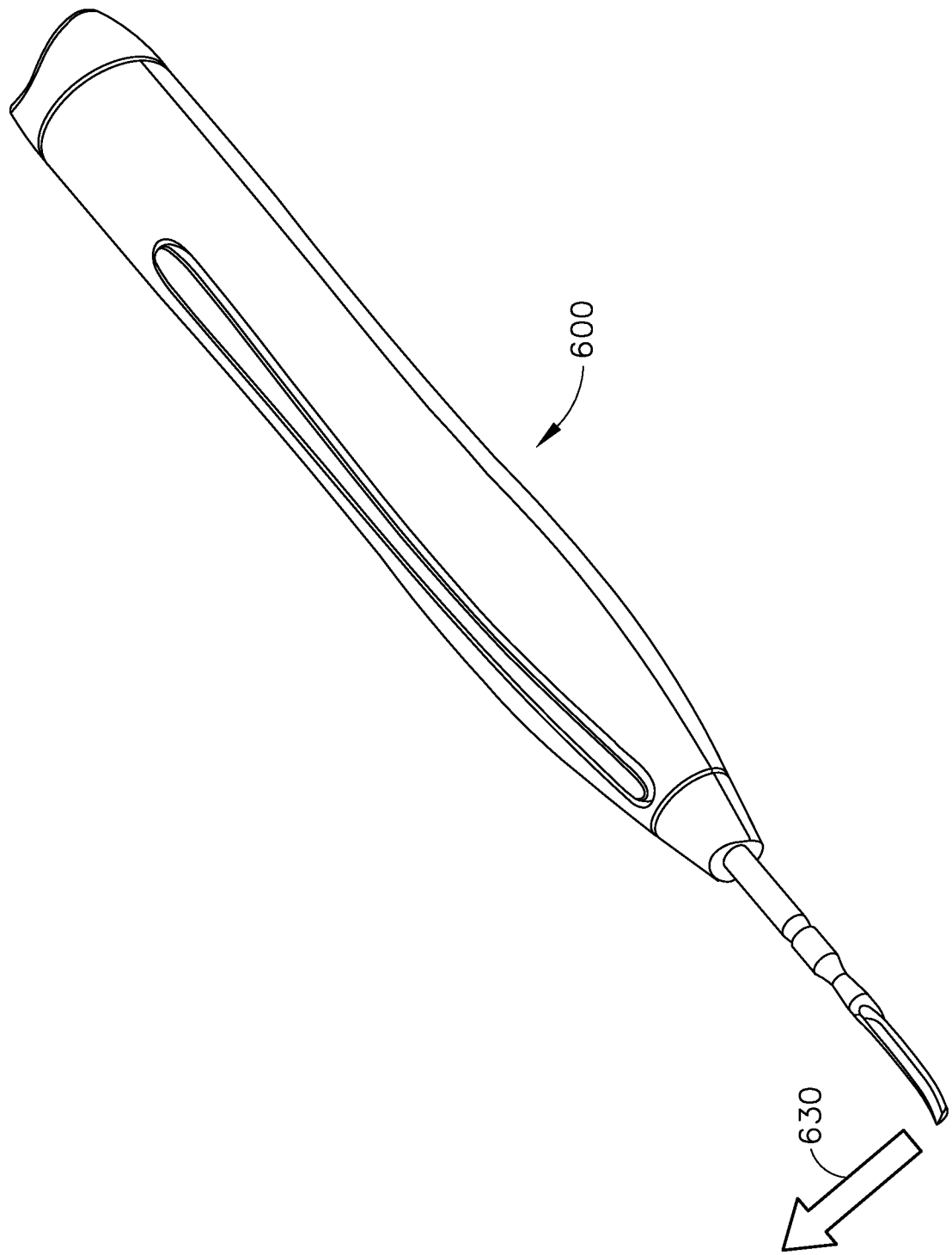
FIG. 10 depicts a perspective view of an exemplary surgical instrument showing a third exemplary gesture.

In the present example, module (590) comprises a non-volatile solid state memory module that is operable to store one or more configuration datas. For example, module (590) may contain a configuration data having one or more gesture profiles to be used by a control module, such as control module (40) described in reference to FIG. 1, of surgical instrument (500) to compare the user's movement of instrument (500) with the expected gesture profiles defined by the configuration data. Such a comparison may be used to give feedback to the user as the procedure is progressing and/or to adjust settings of instrument (500), as will be described in greater detail below in reference to FIGS. 11-12. When end effector (550) is coupled to instrument (500), module (590) interfaces with the control module of instrument (500) to provide the configuration data to the control module. By way of example only, FIGS. 8-10 depict an instrument (600) with an end effector (650) having configuration data for three different gesture profiles with three different energy settings. As shown in FIG. 8, when instrument (600) is used in a manner that indicates a sweeping or digging motion in accordance with arrow (610), a first energy setting may be applied to the transducer of instrument (600). As shown in FIG. 9, when instrument (600) is used in a manner that indicates a pressing motion in accordance with arrow (620), a second energy setting is applied to the transducer of instrument (600). As shown in FIG. 10, when instrument (600) is used in a manner that indicates a scraping motion in accordance with arrow (630), a third energy setting is applied to the transducer of instrument (600). Of course still further motions and/or combination of motions will be apparent to one of ordinary skill in the art in view of the teachings herein.

It should be understood that, in some versions, each end effector (550) may include a configuration data for a single gesture profile and a single corresponding energy setting within module (590). Accordingly, attachment of different end effectors (550) provides different configuration datas to the control module for individual gesture profiles and energy setting. Thus, a user can be provided with a number of end effectors (550) that may be associated with different gestures to be performed. Such end effectors (550) may include one or more visual indicators to distinguish which end effector is associated with the various gestures. By way of example only, keyblock (570) and/or other portions of end effector (550) may vary by color. Alternatively, a textual or graphical symbol may be included on end effector (550) to distinguish the end effectors (550). Of course still other indicators will be apparent to one of ordinary skill in the art in view of the teachings herein. In some versions, a set of these end effectors (550) may be provided in a kit for a procedure such that a user can readily swap out end effectors (550) in order to accomplish a given procedure.

In some instances, module (590) may be accessible to a user such that a user can define the configuration data for module (590). For instance, it may be preferable to the user to be able to define the gesture profiles and energy settings for the configuration data. Such user-defined configuration data may be modified by a user interface (such as a computer program and interface unit that interfaces with module (590), user interface (60), etc.) to define the gesture profiles and energy settings. In some versions, defining the gesture profiles and energy settings may be based upon the monitoring the output of sensors from instrument (500) as the user uses instrument (500) during a configuration mode where the user sets the energy setting and performs the gesture to be associated with the energy setting. In yet other versions, module (590) may incorporate other components and/or process data from such other components, such as end effector sensor (98) and/or accelerometer (234) described above. Still other end effectors (550) and/or modules (590) will be apparent to one of ordinary skill in the art in view of the teachings herein.

V. Exemplary Control Methods

As noted above, in some versions it may be preferable to provide feedback to a user and/or adjust settings of a surgical instrument (10, 150, 200, 400, 500, 600) based upon the output of sensors (30, 80, 98, 232, 234, 300, 410) that interface with a control module (40) and/or based upon a comparison to the one or more gesture profiles contained within a configuration data. Such feedback and/or adjustments may reduce the learning curve for a user and/or expedite the performance of procedures by not requiring that the user manually adjust the energy settings for the surgical instrument (10, 150, 200, 400, 500, 600) for each gesture profile. In addition, if the instrument (10, 150, 200, 400, 500, 600) encounters unexpected motions, control module (40) may be configured to adjust the settings of the instrument (10, 150, 200, 400, 500, 600) based upon the input from the various sensors (30, 80, 98, 232, 234, 300, 410). Accordingly, an exemplary method to adaptively control the instrument (10, 150, 200, 400, 500, 600) will now be described.

Figure 11:
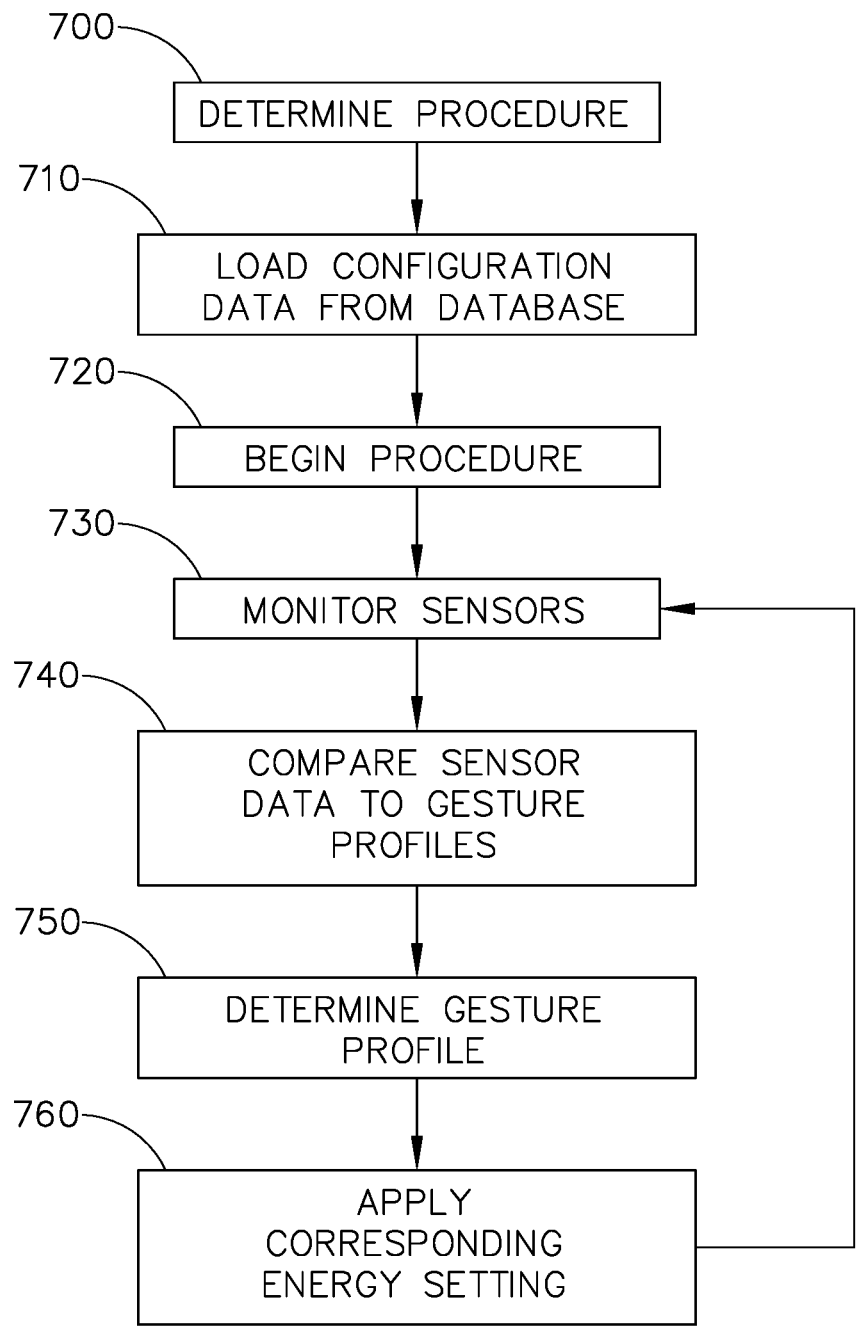
FIG. 11 depicts a flowchart of exemplary steps for monitoring the motion of an exemplary surgical instrument.

FIG. 11 depicts an exemplary method for controlling an instrument, such as instruments (10, 150, 200, 400, 500, 600), with control module (40) based upon the manner in which a user uses instrument (10, 150, 200, 400, 500, 600) and adjusts the energy settings based upon various predefined gesture profiles, such as those shown in FIG. 8-10. In the present example, control module (40) receives data from sensors (30, 80, 98, 232, 234, 300, 410) and compares the sensor data to one or more gesture profiles from configuration data. The one or more gesture profiles each have a corresponding energy setting that control module (40) applies to the energy component, such as energy component (20) or transducer (190), of instrument (10, 150, 200, 400, 500, 600). The configuration data is stored in a storage device, such as module (590) and/or storage device (50), and is communicatively coupled to control module (40).

As shown in FIG. 11, the method begins at block (700) by determining which procedure is to be performed (e.g., plastic surgery, orthopedic surgery, etc.). For example, an end effector, such as end effector (550), may be configured to include configuration data for instrument (10, 150, 200, 400, 500, 600) for a specific task or procedure. Accordingly, the coupling of the end effector to a surgical instrument (10, 150, 200, 400, 500, 600) may determine the procedure simply by control module (40) receiving the configuration data when the end effector is coupled to instrument (10, 150, 200, 400, 500, 600). In another version, a database of procedures or tasks may be stored on storage device (50) and the various procedures or tasks may be selectable via a user interface, such as user interface (60). Such procedures or tasks may have corresponding configuration data that may be loaded at block (710). Still other ways to determine the procedure to be performed will be apparent to one of ordinary skill in the art in view of the teachings herein. Of course it should be understood that block (700) may be omitted as well.

At block (710), the configuration data is loaded from a storage device and/or database. In the present example, the configuration data includes one or more gesture profiles, such as those shown in FIGS. 8-10, as well as a corresponding energy setting for each gesture profile. For example, the transducer may be configured to operate at a first energy level when performing the sweeping motion shown in FIG. 8, while the transducer may be configured to operate at a second, different energy level when performing the pressing motion shown in FIG. 9. In addition, or in the alternative, the energy levels for the transducer may also be varied based upon the procedure to be performed. For instance, procedures involving delicate or sensitive tissue areas may include energy settings that limit the transducer to low energy levels while procedures involving tough or thick tissue may include energy settings that employ high energy levels for the transducer. Of course it should be understood that such energy settings and gesture profiles are not limited to ultrasonic surgical instruments, but may be applied to other surgical instruments, such as endocutters, graspers, cutters, staplers, clip appliers, access devices, drug/gene therapy delivery devices, and/or other energy delivery devices using RF, laser, etc. In some versions, the configuration data may be loaded from module (590) of end effector (550) when end effector (550) is coupled to instrument (500). Alternatively, such configuration data may be pre-loaded on a storage device, such as storage device (50), of the instrument (10, 150, 200, 400, 500, 600), may be loaded from a remote source, and/or otherwise.

With the configuration data loaded, the user begins the procedure at block (720). By way of example only, the procedure may begin when the user positions the instrument (10, 150, 200, 400, 500, 600) in an initial gesture position and/or when a user operates an activation button or other feature, such as trigger (168). In the instance of an initial gesture position, the configuration data may include a plurality of initial orientation positions for surgical instrument (10, 150, 200, 400, 500, 600) that correspond to various desired outcomes or procedures. For example, these initial orientation positions may include positions for cutting, coagulating, scraping, pressing, sweeping, etc. Data from sensors (30, 232, 234, 300, 410) indicating the orientation of instrument (10, 150, 200, 400, 500, 600) is transmitted to control module (40) and compared to the various initial orientation positions to determine which initial orientation position is intended by the user. Once an initial orientation position is determined, the energy component, such as energy component (20) or transducer (190), is activated at a corresponding energy setting for that initial orientation position. In addition, or in the alternative, the activation button or other feature may be provided to selectively activate instrument (10, 150, 200, 400, 500, 600) once the user has positioned instrument (10, 150, 200, 400, 500, 600) in an initial orientation position and/or to activate instrument (10, 150, 200, 400, 500, 600) at a predetermined initial energy level regardless of the orientation of instrument (10, 150, 200, 400, 500, 600). In some versions the energy component of the instrument (10, 150, 200, 400, 500, 600) may remain inactive even after the activation button is operated by the user and will not be activated until control module (40) determines that one of the gesture profiles of configuration data is performed, as will be described below, or, in some versions, until a specific start gesture (e.g., a motion indicating the device should activate) is performed. Of course the foregoing is merely optional.

Once the user has begun the procedure, control module (40) monitors sensors (30, 80, 98, 232, 234, 300, 410) at block (730). For example, control module (40) monitors the orientation and/or movement of instrument (10, 150, 200, 400, 500, 600) via the output from first sensor (30), gyroscope (232), accelerometer (234), orientation sensor (300), and/or orientation sensor (410). Accordingly, control module (40) can utilize the orientation and/or movement data to determine the various gestures and/or rapidity of movements of instrument (10, 150, 200, 400, 500, 600) performed by the user. In addition, or in the alternative, control module (40) monitors the force applied to an end effector via second sensor (80) and/or end effector sensor (98), as will be discussed in greater detail below in reference to FIG. 12. Of course it should be understood that other sensors, such as temperature sensors, Hall Effect sensors, etc., may be monitored by control module (40) such that control module (40) may further adjust the energy setting for the energy component or otherwise modify the settings for instrument (10, 150, 200, 400, 500, 600), in real time as instrument (10, 150, 200, 400, 500, 600) is being used, based on how instrument (10, 150, 200, 400, 500, 600) is being used.

At block (740), the sensor data from block (730) is compared to the various gesture profiles from the configuration data. By way of example only, the output from sensors (30, 80, 98, 232, 234, 300, 410) over a predetermined period of time is compared to expected output for sensors (30, 80, 98, 232, 234, 300, 410) for each of the various gesture profiles. At block (750), control module (40) determines which gesture profile from the configuration data correlates the most to the output from sensors (30, 80, 98, 232, 234, 300, 410). For example, if gyroscope (232) indicates that the orientation of instrument (10, 150, 200, 400, 500, 600) remains substantially vertical and accelerometer (234) indicates a downward motion of instrument (10, 150, 200, 400, 500, 600), then control module (40) would determine that the pressing motion shown in FIG. 9 is occurring and the corresponding gesture profile would be determined. Similar determinations for a sweeping motion (FIG. 8) and/or a scraping motion (FIG. 10) may be made utilizing the orientation and movement information from sensors (30, 232, 234, 300, 410). With the gesture profile determined, control module (40) applies the corresponding energy setting at block (760) such that the output from the energy component is appropriate for the determined gesture. Control module (40) then returns to monitoring the sensors (30, 80, 98, 232, 234, 300, 410) at block (730). The method can continue to adjust the energy settings according to the various gesture profiles indicated by the outputs from sensors (30, 80, 98, 232, 234, 300, 410) as the user performs the procedure. Accordingly, the user may simply adjust their gestures using instrument (10, 150, 200, 400, 500, 600) to change the energy settings on the fly. In some versions, the user may release the activation button or other feature to deactivate instrument (10, 150, 200, 400, 500, 600), reorient instrument (10, 150, 200, 400, 500, 600) to a different position indicative of a different energy setting, and reactivate instrument (10, 150, 200, 400, 500, 600) to proceed with the procedure with the new energy setting.

In some versions, a predetermined threshold value for an anomalous acceleration or deceleration may be set in configuration data. While instrument (10, 150, 200, 400, 500, 600) is operating in accordance with the gesture profiles, the energy setting remains unaltered. If the output from accelerometer (234) indicates that this anomalous acceleration or deceleration threshold value has occurred, such as during block (730) when control module (40) is monitoring sensors (30, 80, 98, 232, 234, 300, 410) and/or during block (740) when the output from sensors (30, 80, 98, 232, 234, 300, 410) is compared to the various gesture profiles, then control module (40) is configured to reduce the energy setting or, in some versions, to deactivate the energy component of instrument (10, 150, 200, 400, 500, 600) entirely. Once the anomalous acceleration or deceleration ceases and/or sensors (30, 80, 98, 232, 234, 300, 410) indicate a normal gesture profile, the energy component is reactivated or the energy setting is returned to the value corresponding to the indicated gesture profile. Thus, if the user inadvertently loses control of instrument (10, 150, 200, 400, 500, 600) during a procedure or encounters unexpectedly soft or dense tissue, control module (40) may be operable to reduce or stop the ultrasonic oscillation of the blade. Of course it should be understood that the foregoing is not limited to ultrasonic surgical instruments, but may be applied to other surgical instruments, such as endocutters, graspers, cutters, staplers, clip appliers, access devices, drug/gene therapy delivery devices, and/or other energy delivery devices using RF, laser, etc.

Figure 12:
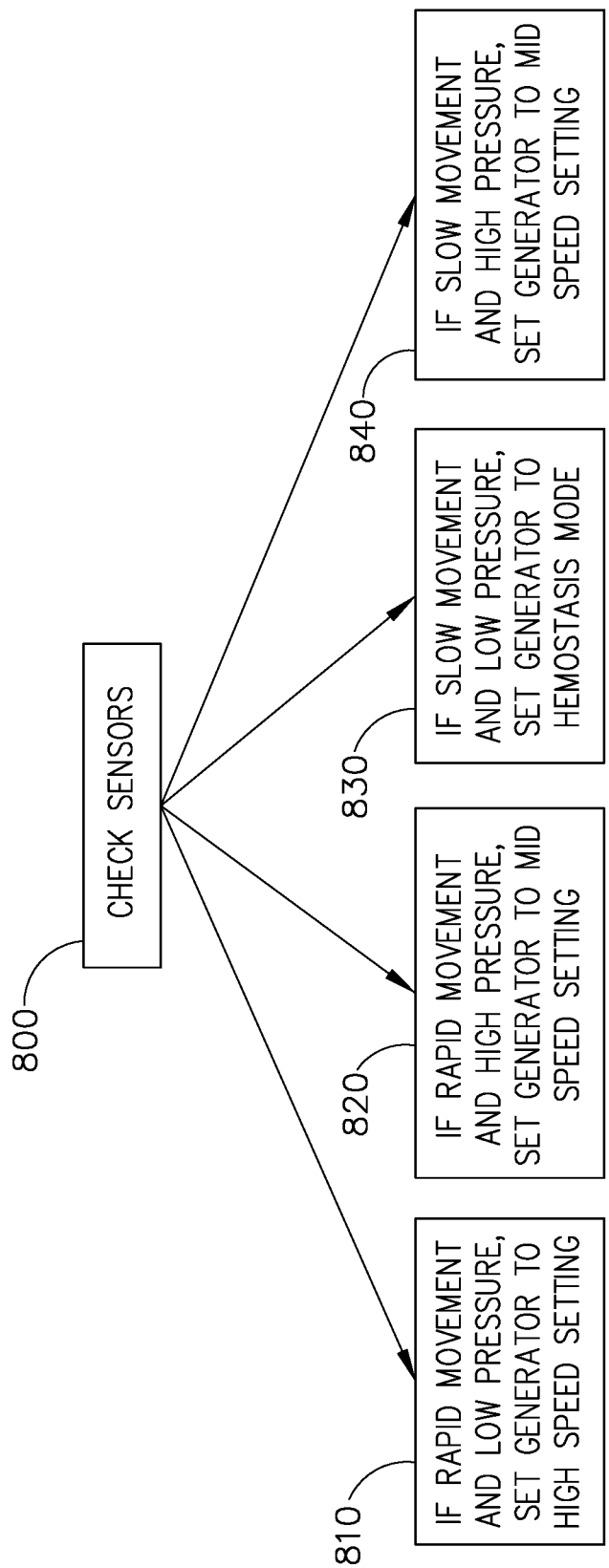
FIG. 12 depicts a flowchart of exemplary steps performed in response to the monitoring of one or more sensors.

While the foregoing described applying various energy settings corresponding to various gesture profiles, FIG. 12 depicts an alternative set of energy settings that may be determined by control module (40) in response to the monitoring of sensors (30, 80, 98, 232, 234, 300, 410) based upon the speed of movement of instrument (10, 150, 200, 400, 500, 600) and the force applied to the blade of the end effector. In the present example, the movement of instrument (10, 150, 200, 400, 500, 600) is measured via an accelerometer, such as accelerometer (234) and the force applied to the blade is measured via a force sensor, such as second sensor (80) and/or end effector sensor (98). At block (800), control module (40) checks the output from sensors (80, 98, 234). If sensors (80, 98, 234) indicate rapid movement of instrument (10, 150, 200, 400, 500, 600) with low force or pressure on the blade, then the energy setting for the energy component is set to a high speed setting for tissue dissection at block (810). If sensors (80, 98, 234) indicate rapid movement of instrument (10, 150, 200, 400, 500, 600) with high force or pressure on the blade, then the energy setting for the energy component is set to a mid-range setting at block (820) for cutting through tough tissue or vessels. If sensors (80, 98, 234) indicate slow movement of instrument (10, 150, 200, 400, 500, 600) with low force or pressure on the blade, then the energy setting for the energy component is set to a hemostasis mode setting at block (830) for sealing vessels. If sensors (80, 98, 234) indicate slow movement of instrument (10, 150, 200, 400, 500, 600) with high force or pressure on the blade, then the energy setting for the energy component is set to a mid-range setting at block (840) for cutting through tough tissue or vessels. Control module (40) may continually check the sensors at block (800) and determine the appropriate energy setting at blocks (810, 820, 830, 840). It should further be understood that in some versions the energy settings shown in FIG. 12 may be incorporated into the method shown in FIG. 11 to replace blocks (730, 740, 750, 760). Of course other settings based upon varying force and/or movement data will be apparent to one of ordinary skill in view of the teachings herein.

In addition or in the alternative to adjustment of the energy settings, in some versions instrument (10, 150, 200, 400, 500, 600) may be configured to provide user feedback based upon a comparison of the user's gestures to an expected user gesture profile. For example, if a sweeping motion is expected and the output from sensors (30, 80, 98, 232, 234, 300, 410) indicates that the user is performing the sweeping motion, but doing so too slowly, control module (40) may be configured to provide audible and/or visual feedback via user interface (60) to the user to indicate that the user is going too slowly. By way of example only, a periodic click may be emitted from a speaker when instrument (10, 150, 200, 400, 500, 600) is operating normally and the periodic click slows down when the user is proceeding too slowly with the gestural movement. If the user is proceeding too rapidly, the periodic click may increase in speed. Of course other variations for the audible feedback will be apparent to one of ordinary skill in the art in view of the teachings herein. In addition, or in the alternative, a visual indicator may be provided to indicate whether the user is proceeding within a preferred operating range for the gesture or is going too slow or too fast. For instance, an array of LEDs indicating the relative speed may be provided. In addition, or in the alternative, a continuous line or periodic graphical display may be provided on a screen in a similar manner to an oscilloscope or other graphical display to provide the user with visual feedback of their performance relative to a preferred operating range. Control module (40) may be further configured in accordance with at least some of the teachings of U.S. Pat. No. 9,681,884, entitled "Surgical Instrument with Stress Sensor," issued Jun. 20, 2017, the disclosure of which is incorporated by reference herein. Such audible and/or visual feedback may hasten a user's understanding of the preferred operating motions for various gestures, thereby reducing the learning curve for instrument (10, 150, 200, 400, 500, 600). Still other user feedback and/or adjustments to instrument (10, 150, 200, 400, 500, 600) will be apparent to one of ordinary skill in the art in view of the teachings herein.

VI. Miscellaneous

As noted above, a storage device may be used to store operating parameters, other data, and/or control algorithms, etc. associated with the various kinds of surgical instruments referred to herein. Such information may be preloaded and/or later updated; and may dictate performance characteristics of the surgical instrument. For instance, software/firmware/information on the storage device may influence power delivery from a generator or other power source, which may in turn affect the performance of the end effector as driven by the power source. In some systems, a generator, power source, control module, and/or other component provides a baseline functionality for the surgical instrument; while software/firmware/information on the storage device provides enhanced functionality (e.g., active dampening, surgeon gesture recognition, enhanced user feedback, etc.). It should be understood that a storage device may take any suitable form, including but not limited to a chip, card, or other type of storage medium as will be apparent to those of ordinary skill in the art in view of the teachings herein. It should also be understood that the storage device may be located in any suitable location within the system. By way of example only, the storage device may be located in a removable cartridge, such as the various removable cartridges described in U.S. Patent Appln. Ser. No. 13/426,760, entitled "Method and Apparatus for Programming Modular Surgical Instrument," filed Mar. 22, 2012, now U.S. Pat. No. 9,364,249, issued Jun. 14, 2016, the disclosure of which is incorporated by reference herein, the disclosure of which is incorporated by reference herein. As another merely illustrative example, the storage device may be embodied in an online remote server that is in communication with the surgical instrument and/or generator, etc., such as in the system described in U.S. Patent Appln. Ser. No. 13/426,792, entitled "Surgical Instrument Usage Data Management," filed Mar. 22, 2012, now abandoned, the disclosure of which is incorporated by reference herein, the disclosure of which is incorporated by reference herein. As yet another merely illustrative example, the storage device may be included as either an integral component or a removable component of the end effector, shaft, handpiece, cable, and/or other part of the surgical instrument. Various other suitable locations for a storage device will be apparent to those of ordinary skill in the art in view of the teachings herein. It should also be understood that the storage device may store surgeon usage data, patient data, and/or other kinds of data as described herein, such that the storage device may receive additional data during use of the surgical instrument.

In some versions, a manufacturer or seller of a surgical instrument provides the surgical instrument as a single use instrument, with the appropriate software/firmware/information preloaded on the storage device for the single use. In some such versions, the software/firmware/information is inaccessible or inoperable after the surgical instrument is used for a predetermined number of uses. For instance, if the instrument is designed for a specified number of uses, the software/firmware/information may be at least partially deleted or disabled at some point after the predefined design life is exceeded. In the case where either the manufacturer or another party chooses to reprocess/resterilize the device beyond the predefined design life, the reprocessed/resterilized surgical instrument may still be at least partially operable, but with reduced functionality. For instance, a surgeon may still be able to suitably use the reprocessed/resterilized surgical instrument, but the instrument may lack enhanced functionality (e.g., active dampening, surgeon gesture recognition, enhanced user feedback, etc.) that was otherwise originally provided through the software/firmware/information stored in the storage device. In some versions, the storage device allows the manufacturer or seller to segment the performance of the instrument according to the functional needs of the customer. If the customer only needs limited functionality to perform specific surgeries such cholecystectomy, then the storage device will be loaded with the appropriate software/firmware/information. If the customer needs enhanced performance for difficult surgeries or to expand the potential operating performance of the device if the surgery is more difficult than anticipated, then the storage device may be loaded accordingly. In either case, some versions may permit a manufacturer or seller to adjust the functionality of the surgical instrument to meet the needs of the customer with the customer defined functionality from software/firmware/information on the storage device; and to meet a different set of customer defined needs without the enhanced functionality.

Finally, it should be understood that software/firmware/information in a storage device as described herein need not necessarily be influenced by any kind of sensors in the surgical instrument. For instance, the surgical instrument may simply lack sensors altogether; or the storage device may not be in communication with sensors.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an end effector configured to operate at a plurality of energy settings;
   (b) a control module;
   (c) a storage device communicatively coupled with the control module, wherein the storage device comprises a plurality of configuration data sets, wherein each configuration data set comprises a respective gesture profile and a corresponding energy setting, wherein the control module is configured to receive a selected configuration data set from the storage device;
   (d) a movement sensor configured to measure a movement of the apparatus; and
   (e) a force sensor configured to measure a force applied to the end effector, wherein the control module is configured to receive a first output of the measured force and the measured movement from the force sensor and the movement sensor, respectively;
   wherein the control module is configured to compare the first output to a first gesture profile of the selected configuration data set; and
   wherein the control module is configured to set the energy setting of the end effector to a first corresponding energy setting in response to a correlation between the first output and the first gesture profile of the selected configuration data set.

2. The apparatus of claim 1, wherein the end effector is configured to deliver RF energy.

3. The apparatus of claim 1, wherein the end effector is configured to deliver laser energy.

4. The apparatus of claim 1, wherein the apparatus further comprises a power source.

5. The apparatus of claim 4, wherein the apparatus further comprises a body, wherein the power source is housed within the body.

6. The apparatus of claim 4, wherein the apparatus further comprises a body, wherein the power source is external relative to the body.

7. The apparatus of claim 1, wherein the end effector is configured to vibrate at ultrasonic frequencies.

8. The apparatus of claim 7, wherein the apparatus further comprises an ultrasonic transducer configured to drive the end effector at the plurality of energy settings, wherein each energy setting comprises one or both a frequency or an amplitude of vibrational waves generated by the ultrasonic transducer.

9. The apparatus of claim 8, wherein the apparatus further comprises a waveguide operable to communicate vibration waves generated from the ultrasonic transducer toward the end effector.

10. The apparatus of claim 1, wherein the apparatus further comprises a shaft extending proximally from the end effector.

11. The apparatus of claim 7, wherein the force sensor is coupled to the shaft.

12. The apparatus of claim 11, further comprising a body, wherein the shaft is coupled with the body, wherein the force sensor is located within the body.

13. The apparatus of claim 1, further comprising an orientation sensor, wherein the control module is configured to receive a second output from the orientation sensor, wherein the control module is configured to compare a combination of the first output and the second output to the first gesture profile of the selected configuration data set, and wherein the control module is configured to set the energy setting of the end effector to the first corresponding energy setting in response to a correlation between the combination of the first output and the second output to the first gesture profile of the selected configuration data set.

14. The apparatus of claim 13, wherein the orientation sensor is associated with the end effector.

15. The apparatus of claim 13, wherein the orientation sensor includes at least one of a gyroscope or an inclinometer.

16. The apparatus of claim 1, further comprising a body, wherein the end effector is configured to selectively couple with the body.

17. The apparatus of claim 1, wherein the force sensor is configured to measure a force orientation applied to the end effector, wherein the control module is configured to receive a second output of the measured force orientation from the force sensor, wherein the control module is configured to compare a combination of the first output and the second output to the first gesture profile of the selected configuration data set, and wherein the control module is configured to set the energy setting of the end effector to the first corresponding energy setting in response to a correlation between the combination of the first output and the second output to the first gesture profile of the selected configuration data set.

18. A method for controlling a surgical instrument comprising an end effector, a movement sensor operable to detect movement of the end effector, a force sensor operable to detect a force applied to the end effector, a storage device, and a control module, an interface in communication with the control module, wherein the end effector is capable of operating at a plurality of energy settings, wherein the control module is operable to set an energy setting for the end effector, wherein the force sensor is communicatively coupled to the control module, wherein the storage device comprises a plurality of configuration data sets, wherein each configuration data set comprises a plurality of gesture profiles and a plurality of corresponding energy settings, wherein each gesture profile of the plurality of gesture profiles is associated with a corresponding energy setting of the plurality of energy settings, wherein the control module is configured to receive data from the force sensor, the method comprising the steps of:
- (a) receiving a selection, via the interface, of a configuration data set from the plurality of configuration data sets;
- (b) receiving an output of the force sensor and the movement sensor by the control module;
- (c) receiving the plurality of gesture profiles and the plurality of corresponding energy settings associated with the selected configuration data set from the storage device by the control module; and
- (d) setting the end effector to a first corresponding energy setting associated with a first gesture profile in response to a correlation between the first gesture profile and the output of the force sensor and the movement sensor, wherein the first corresponding energy setting provides a first energy output by the end effector.

19. The method of claim 18, further comprising adjusting the first corresponding energy setting based upon the output of the force sensor.

20. An apparatus comprising:
- (a) a control module;
- (b) a storage device communicatively coupled with the control module, wherein the storage device comprises a plurality of configuration data sets, wherein each configuration data set comprises a respective gesture profile and a corresponding energy setting, wherein the control module is configured to receive a selected configuration data set from the storage device;
- (c) an end effector configured to operate at a plurality of energy settings;
- (d) a movement sensor in communication with the control module; (e) a force sensor in communication with the control module, wherein the force sensor is configured to measure an external force acting on the end effector;

wherein the control module is configured to compare a combination of data from the movement sensor and the force sensor to a first gesture profile of the selected configuration data set; and wherein the control module is configured to set the energy setting of the end effector to a first corresponding energy setting in response to a correlation between the combination of data from the movement sensor and the force sensor to the first gesture profile of the selected configuration data set.

* * * * *